United States Patent
Owen et al.

(10) Patent No.: US 8,192,053 B2
(45) Date of Patent: Jun. 5, 2012

(54) HIGH EFFICIENCY SOLID-STATE LIGHT SOURCE AND METHODS OF USE AND MANUFACTURE

(75) Inventors: Mark D. Owen, Beaverton, OR (US); Tom McNeil, Portland, OR (US); Francois Vlach, Portland, OR (US)

(73) Assignee: Phoseon Technology, Inc., Hillsboro, OR (US)

( * ) Notice: Subject to any disclaimer, the term of this patent is extended or adjusted under 35 U.S.C. 154(b) by 215 days.

(21) Appl. No.: 10/984,589

(22) Filed: Nov. 8, 2004

(65) Prior Publication Data
US 2005/0152146 A1   Jul. 14, 2005

Related U.S. Application Data

(63) Continuation-in-part of application No. PCT/US03/14625, filed on May 8, 2003.

(51) Int. Cl.
*F21V 29/00* (2006.01)

(52) U.S. Cl. ........ 362/294; 362/573; 362/227; 362/241; 362/301; 362/373

(58) Field of Classification Search .............. 362/294, 362/573, 227, 230, 231, 241, 301, 373, 800; 433/29; 315/247, 246, 209 R, 224, 292; 361/18, 62
See application file for complete search history.

(56) References Cited

U.S. PATENT DOCUMENTS

| | | | |
|---|---|---|---|
| 3,586,959 A | 6/1971 | Eccles et al. | |
| 3,936,686 A * | 2/1976 | Moore | 313/36 |
| 4,011,575 A | 3/1977 | Groves | |
| 4,194,814 A | 3/1980 | Fischer et al. | |
| 4,435,732 A | 3/1984 | Hyatt | |
| 4,439,910 A | 4/1984 | Vasudev | |
| 4,504,776 A * | 3/1985 | Haville | 323/288 |
| 4,530,040 A * | 7/1985 | Petterson | 362/188 |
| 4,544,642 A * | 10/1985 | Maeda et al. | 501/88 |
| 4,595,289 A | 6/1986 | Feldman et al. | |
| 4,680,644 A | 7/1987 | Shirato et al. | |
| 4,684,801 A | 8/1987 | Carroll et al. | |

(Continued)

FOREIGN PATENT DOCUMENTS

DE          8815418          2/1989
(Continued)

OTHER PUBLICATIONS

Electromagnetic spectrum (http://www.brocku.ca/earthsciies/people/gfinn/optical/spectrum.gif).*

(Continued)

*Primary Examiner* — Jong-Suk (James) Lee
*Assistant Examiner* — Mark Tsidulko
(74) *Attorney, Agent, or Firm* — Marger Johnson & McCollom PC

(57) ABSTRACT

A high-intensity light source is formed by a micro array of a semiconductor light source such as a LEDs, laser diodes, or VCSEL placed densely on a liquid or gas cooled thermally conductive substrate. The semiconductor devices are typically attached by a joining process to electrically conductive patterns on the substrate, and driven by a microprocessor controlled power supply. An optic element is placed over the micro array to achieve improved directionality, intensity, and/or spectral purity of the output beam. The light module may be used for such processes as, for example, fluorescence, inspection and measurement, photopolymerzation, ionization, sterilization, debris removal, and other photochemical processes.

9 Claims, 16 Drawing Sheets

U.S. PATENT DOCUMENTS

| | | | |
|---|---|---|---|
| 4,685,139 A | 8/1987 | Masuda et al. | |
| 4,734,714 A | 3/1988 | Takasu et al. | |
| 5,003,357 A | 3/1991 | Kim et al. | |
| 5,018,853 A | 5/1991 | Hechel et al. | |
| 5,067,799 A | 11/1991 | Gold et al. | |
| 5,150,623 A | 9/1992 | Woods | |
| 5,195,102 A | 3/1993 | McLean et al. | |
| 5,296,724 A | 3/1994 | Ogata et al. | |
| 5,365,084 A | 11/1994 | Cochran et al. | |
| 5,397,867 A * | 3/1995 | Demeo | 200/5 A |
| 5,418,384 A | 5/1995 | Yamana et al. | |
| 5,424,544 A | 6/1995 | Shelton et al. | |
| 5,436,710 A | 7/1995 | Uchiyama | |
| 5,449,926 A | 9/1995 | Holm et al. | |
| 5,479,029 A | 12/1995 | Ikawa et al. | |
| 5,487,662 A | 1/1996 | Kipke et al. | |
| 5,490,049 A | 2/1996 | Montalan et al. | |
| 5,522,225 A | 6/1996 | Eskandari | |
| 5,554,849 A | 9/1996 | Gates | |
| 5,555,038 A * | 9/1996 | Conway | 351/159 |
| 5,564,819 A | 10/1996 | Yamaguchi | |
| 5,568,136 A | 10/1996 | Hochstein et al. | |
| 5,623,510 A | 4/1997 | Hamilton et al. | |
| 5,632,551 A | 5/1997 | Roney et al. | |
| 5,633,629 A | 5/1997 | Hochstein | |
| 5,660,461 A | 8/1997 | Ignatius et al. | |
| 5,661,645 A | 8/1997 | Hochstein | |
| 5,670,780 A | 9/1997 | Lewis | |
| 5,698,866 A | 12/1997 | Doiron et al. | |
| 5,705,788 A | 1/1998 | Beyer et al. | |
| 5,715,270 A | 2/1998 | Zediker et al. | |
| 5,719,589 A | 2/1998 | Norman et al. | |
| 5,724,062 A | 3/1998 | Hunter | |
| 5,777,729 A | 7/1998 | Aiyer et al. | |
| 5,782,555 A | 7/1998 | Hochstein | |
| 5,783,909 A | 7/1998 | Hochstein | |
| 5,784,006 A | 7/1998 | Hochstein | |
| 5,785,418 A | 7/1998 | Hochstein | |
| 5,806,965 A | 9/1998 | Deese | |
| 5,857,767 A | 1/1999 | Hochstein | |
| 5,877,899 A | 3/1999 | Stern et al. | |
| 5,880,828 A | 3/1999 | Nakamura et al. | |
| 5,886,313 A | 3/1999 | Krause et al. | |
| 5,892,579 A | 4/1999 | Elyasaf et al. | |
| 5,910,706 A | 6/1999 | Stevens et al. | |
| 5,936,353 A * | 8/1999 | Triner et al. | 315/112 |
| 5,940,683 A | 8/1999 | Holm et al. | |
| 6,033,087 A * | 3/2000 | Shozo et al. | 362/244 |
| 6,045,240 A | 4/2000 | Hochstein | |
| 6,058,012 A * | 5/2000 | Cooper et al. | 361/704 |
| 6,065,854 A | 5/2000 | West et al. | |
| 6,077,073 A | 6/2000 | Jacob | |
| 6,078,148 A | 6/2000 | Hochstein | |
| 6,088,185 A | 7/2000 | Ratliff et al. | |
| 6,115,184 A | 9/2000 | Hubble, III et al. | |
| 6,118,383 A | 9/2000 | Hegyi | |
| 6,141,040 A | 10/2000 | Toh | |
| 6,155,699 A * | 12/2000 | Miller et al. | 362/293 |
| 6,160,354 A | 12/2000 | Ravinski et al. | |
| 6,163,036 A | 12/2000 | Taninaka et al. | |
| 6,200,134 B1 * | 3/2001 | Kovac et al. | 433/29 |
| 6,222,207 B1 | 4/2001 | Carter-Coman et al. | |
| 6,224,216 B1 | 5/2001 | Parker et al. | |
| 6,232,659 B1 | 5/2001 | Clayton | |
| 6,252,351 B1 | 6/2001 | Koizami et al. | |
| 6,258,618 B1 | 7/2001 | Lester | |
| 6,273,596 B1 | 8/2001 | Parkyn, Jr. | |
| 6,288,497 B1 | 9/2001 | Chang et al. | |
| 6,290,382 B1 | 9/2001 | Bourn et al. | |
| 6,291,839 B1 | 9/2001 | Lester | |
| 6,299,329 B1 | 10/2001 | Mui et al. | |
| 6,318,886 B1 * | 11/2001 | Stopa et al. | 362/555 |
| 6,318,996 B1 | 11/2001 | Melikechi et al. | |
| 6,319,425 B1 * | 11/2001 | Tasaki et al. | 252/301.36 |
| 6,325,524 B1 | 12/2001 | Weber et al. | |
| 6,328,456 B1 | 12/2001 | Mize | |
| 6,329,758 B1 | 12/2001 | Salam | |
| 6,330,017 B1 | 12/2001 | Suzuki | |
| 6,340,868 B1 | 1/2002 | Lys et al. | |
| 6,342,402 B1 | 1/2002 | Tajiri et al. | |
| 6,346,771 B1 | 2/2002 | Salem | |
| 6,357,904 B1 | 3/2002 | Kawashima | |
| 6,366,017 B1 * | 4/2002 | Antoniadis et al. | 313/506 |
| 6,367,950 B1 | 4/2002 | Yamada et al. | |
| 6,373,635 B1 | 4/2002 | Fujimoto et al. | |
| 6,375,340 B1 | 4/2002 | Biebl et al. | |
| 6,419,384 B1 * | 7/2002 | Lewis et al. | 362/562 |
| 6,420,199 B1 | 7/2002 | Coman et al. | |
| 6,420,839 B1 * | 7/2002 | Chiang et al. | 315/311 |
| 6,424,399 B1 | 7/2002 | Shimada et al. | |
| 6,428,189 B1 | 8/2002 | Hochstein | |
| 6,439,888 B1 | 8/2002 | Boutoussov et al. | |
| 6,441,873 B2 | 8/2002 | Young | |
| 6,445,124 B1 | 9/2002 | Asai et al. | |
| 6,450,664 B1 | 9/2002 | Kelly | |
| 6,455,930 B1 | 9/2002 | Palanisamy et al. | |
| 6,459,010 B1 | 10/2002 | Carpena | |
| 6,459,919 B1 | 10/2002 | Lys et al. | |
| 6,462,669 B1 | 10/2002 | Pederson | |
| 6,480,389 B1 | 11/2002 | Shie et al. | |
| 6,498,355 B1 | 12/2002 | Harrah et al. | |
| 6,498,423 B1 * | 12/2002 | Bell et al. | 313/24 |
| 6,517,218 B2 | 2/2003 | Hochstein | |
| 6,518,502 B2 | 2/2003 | Hammond et al. | |
| 6,525,335 B1 | 2/2003 | Krames et al. | |
| 6,533,205 B1 | 3/2003 | Kles | |
| 6,534,791 B1 | 3/2003 | Hayashi et al. | |
| 6,536,923 B1 | 3/2003 | Merz | |
| 6,541,800 B2 | 4/2003 | Barnett et al. | |
| 6,545,808 B1 | 4/2003 | Ehbets et al. | |
| 6,547,249 B2 | 4/2003 | Collins, III et al. | |
| 6,554,217 B1 | 4/2003 | Rodriguez | |
| 6,554,451 B1 | 4/2003 | Keuper | |
| 6,561,640 B1 | 5/2003 | Young | |
| 6,561,808 B2 * | 5/2003 | Neuberger | 433/215 |
| 6,573,536 B1 | 6/2003 | Dry | |
| 6,577,332 B2 | 6/2003 | Osawa et al. | |
| 6,578,986 B2 | 6/2003 | Swaris et al. | |
| 6,578,989 B2 | 6/2003 | Osumi et al. | |
| 6,607,286 B2 | 8/2003 | West et al. | |
| 6,630,689 B2 | 10/2003 | Bhat et al. | |
| 6,669,129 B1 | 12/2003 | Shah | |
| 6,670,856 B1 | 12/2003 | Mazzochette | |
| 6,683,421 B1 * | 1/2004 | Kennedy et al. | 315/291 |
| 6,686,581 B2 | 2/2004 | Verhoeckx et al. | |
| 6,708,501 B1 | 3/2004 | Ghoshal et al. | |
| 6,709,749 B1 | 3/2004 | Kumar | |
| 6,713,862 B2 | 3/2004 | Palanisamy et al. | |
| 6,720,859 B2 | 4/2004 | Mazzochette | |
| 6,724,473 B2 | 4/2004 | Leong et al. | |
| 6,736,321 B2 | 5/2004 | Tsikos et al. | |
| 6,739,047 B2 | 5/2004 | Hammond et al. | |
| 6,739,511 B2 | 5/2004 | Tsikos et al. | |
| 6,742,707 B1 | 6/2004 | Tsikos et al. | |
| 6,742,711 B2 | 6/2004 | Tsikos et al. | |
| 6,746,295 B2 | 6/2004 | Sorg | |
| 6,755,647 B2 | 6/2004 | Melikechi et al. | |
| 6,759,664 B2 | 7/2004 | Thompson et al. | |
| 6,759,803 B2 | 7/2004 | Sorg | |
| 6,759,940 B2 | 7/2004 | Mazzochette | |
| 6,794,688 B2 | 9/2004 | Nakatsu et al. | |
| 6,796,502 B2 | 9/2004 | Nogami et al. | |
| 6,796,690 B2 | 9/2004 | Bohlander | |
| 6,796,698 B2 * | 9/2004 | Sommers et al. | 362/555 |
| 6,796,994 B2 | 9/2004 | Ignatius et al. | |
| 6,798,932 B2 | 9/2004 | Kuhara et al. | |
| 6,799,864 B2 | 10/2004 | Bohler et al. | |
| 6,799,967 B2 | 10/2004 | Cao | |
| 6,800,500 B2 | 10/2004 | Coman et al. | |
| 6,801,237 B2 | 10/2004 | Gaudiana et al. | |
| 6,805,466 B1 * | 10/2004 | Ranish | 362/247 |
| 6,806,987 B2 | 10/2004 | Kwasnick et al. | |
| 6,815,724 B2 | 11/2004 | Dry | |
| 6,822,991 B2 | 11/2004 | Collins, III et al. | |
| 6,826,059 B2 | 11/2004 | Bockle et al. | |
| 6,831,303 B2 | 12/2004 | Dry | |
| 6,834,963 B2 | 12/2004 | Kim et al. | |

| | | |
|---|---|---|
| 6,836,081 B2 | 12/2004 | Swanson et al. |
| 6,850,637 B1 | 2/2005 | Burnett |
| 6,857,767 B2 | 2/2005 | Matsui et al. |
| 6,869,635 B2 | 3/2005 | Kobayashi |
| 6,882,331 B2 | 4/2005 | Wu |
| 6,882,782 B2 | 4/2005 | Conzone et al. |
| 6,930,870 B2 | 8/2005 | Nobe et al. |
| 6,937,754 B1 | 8/2005 | Eguchi |
| 6,992,335 B2 | 1/2006 | Ohkawa |
| 6,995,348 B2 | 2/2006 | Bradley et al. |
| 6,995,405 B2 | 2/2006 | Braddell et al. |
| 7,009,165 B2 | 3/2006 | Hehemann et al. |
| 7,071,493 B2 | 7/2006 | Owen et al. |
| 7,102,172 B2 | 9/2006 | Lynch et al. |
| 7,179,670 B2 | 2/2007 | Shelton et al. |
| 7,440,147 B2 * | 10/2008 | Kelsay .......................... 358/474 |
| 2001/0002120 A1 | 5/2001 | Bessendorf et al. |
| 2001/0007498 A1 | 7/2001 | Arai et al. |
| 2001/0030782 A1 | 10/2001 | Trezza |
| 2001/0046652 A1 | 11/2001 | Ostler et al. |
| 2001/0048814 A1 | 12/2001 | Lenmann et al. |
| 2001/0049893 A1 | 12/2001 | Maas et al. |
| 2002/0005826 A1 | 1/2002 | Pederson |
| 2002/0041499 A1 | 4/2002 | Pederson |
| 2002/0053589 A1 | 5/2002 | Owen et al. |
| 2002/0057567 A1 | 5/2002 | Chen |
| 2002/0090184 A1 | 7/2002 | Sayag |
| 2002/0151941 A1 | 10/2002 | Okawa et al. |
| 2002/0176250 A1 | 11/2002 | Bohler et al. |
| 2002/0187454 A1 * | 12/2002 | Melikechi et al. .............. 433/29 |
| 2002/0191396 A1 | 12/2002 | Reiff et al. |
| 2003/0001507 A1 | 1/2003 | Cao |
| 2003/0002282 A1 | 1/2003 | Swaris et al. |
| 2003/0021121 A1 | 1/2003 | Pederson |
| 2003/0031028 A1 | 2/2003 | Murray et al. |
| 2003/0031032 A1 | 2/2003 | Wu et al. |
| 2003/0038943 A1 * | 2/2003 | Almarzouk et al. .......... 356/451 |
| 2003/0062185 A1 | 4/2003 | Hammond et al. |
| 2003/0128552 A1 | 7/2003 | Takagi et al. |
| 2003/0159308 A1 | 8/2003 | Field et al. |
| 2003/0174947 A1 | 9/2003 | Sweetser et al. |
| 2003/0209714 A1 | 11/2003 | Taskar et al. |
| 2003/0218760 A1 | 11/2003 | Tomasi et al. |
| 2003/0218761 A1 | 11/2003 | Tomasi et al. |
| 2003/0230765 A1 | 12/2003 | Dry |
| 2004/0000677 A1 | 1/2004 | Dry |
| 2004/0011457 A1 | 1/2004 | Kobayashi et al. |
| 2004/0026721 A1 | 2/2004 | Dry |
| 2004/0057873 A1 | 3/2004 | Yerazunis et al. |
| 2004/0061079 A1 | 4/2004 | Thompson et al. |
| 2004/0090794 A1 | 5/2004 | Ollett et al. |
| 2004/0101802 A1 | 5/2004 | Scott |
| 2004/0113549 A1 * | 6/2004 | Roberts et al. ................ 313/512 |
| 2004/0119084 A1 | 6/2004 | Hsieh et al. |
| 2004/0134603 A1 | 7/2004 | Kobayashi et al. |
| 2004/0135159 A1 | 7/2004 | Siegel |
| 2004/0141326 A1 | 7/2004 | Dry |
| 2004/0164325 A1 | 8/2004 | Siegel |
| 2004/0166249 A1 | 8/2004 | Siegel |
| 2004/0183078 A1 | 9/2004 | Wang |
| 2004/0196653 A1 | 10/2004 | Clark et al. |
| 2004/0201846 A1 | 10/2004 | Mullani |
| 2004/0201988 A1 | 10/2004 | Allen |
| 2004/0201995 A1 | 10/2004 | Galli |
| 2004/0203189 A1 | 10/2004 | Chen et al. |
| 2004/0206970 A1 | 10/2004 | Martin |
| 2004/0218390 A1 | 11/2004 | Holman et al. |
| 2004/0222433 A1 | 11/2004 | Mazzochette et al. |
| 2004/0238111 A1 | 12/2004 | Siegel |
| 2005/0082480 A1 | 4/2005 | Wagner et al. |
| 2005/0086964 A1 | 4/2005 | Hackman et al. |
| 2005/0087750 A1 | 4/2005 | Braddell et al. |
| 2005/0088209 A1 | 4/2005 | Wessels |
| 2005/0088380 A1 | 4/2005 | Bulovic et al. |
| 2005/0098299 A1 | 5/2005 | Goodson et al. |
| 2005/0218468 A1 | 10/2005 | Owen |
| 2005/0230600 A1 | 10/2005 | Olson et al. |
| 2005/0231713 A1 | 10/2005 | Owen et al. |
| 2005/0253252 A1 | 11/2005 | Owen et al. |
| 2005/0285129 A1 | 12/2005 | Jackson et al. |
| 2006/0216865 A1 | 9/2006 | Owen et al. |

FOREIGN PATENT DOCUMENTS

| | | |
|---|---|---|
| EP | 146998 A1 | 7/1985 |
| EP | 0560605 | 9/1993 |
| EP | 0935145 | 8/1999 |
| EP | 1033229 | 9/2000 |
| EP | 1158761 | 11/2001 |
| EP | 1462069 | 9/2004 |
| EP | 1467416 | 10/2004 |
| EP | 1469529 | 10/2004 |
| EP | 1502752 A2 | 2/2005 |
| EP | 1526581 A2 | 4/2005 |
| EP | 1479270 B1 | 7/2006 |
| GB | 2224374 | 8/1988 |
| GB | 2396331 | 6/2004 |
| GB | 2399162 | 9/2004 |
| JP | 59035492 | 2/1984 |
| JP | 404204333 | 11/1990 |
| JP | 2003268042 * | 9/2003 |
| WO | 9716679 | 5/1997 |
| WO | WO 9808051 * | 2/1998 |
| WO | 0037904 | 6/2000 |
| WO | 0102846 | 1/2001 |
| WO | 0206723 | 1/2002 |
| WO | 0213231 | 2/2002 |
| WO | 0226270 | 4/2002 |
| WO | WO 02069839 | 9/2002 |
| WO | WO 02/086972 | 10/2002 |
| WO | WO 02103411 | 12/2002 |
| WO | WO03059025 | 7/2003 |
| WO | WO03060927 | 7/2003 |
| WO | WO03060928 | 7/2003 |
| WO | WO 03096387 | 11/2003 |
| WO | WO03096387 A2 | 11/2003 |
| WO | WO 2004/009318 | 1/2004 |
| WO | WO2004/011848 | 2/2004 |
| WO | WO2004011848 C2 | 2/2004 |
| WO | WO2004/038759 | 5/2004 |
| WO | WO2004038759 A2 | 5/2004 |
| WO | WO2004038759 A3 | 5/2004 |
| WO | WO 2004/049462 | 6/2004 |
| WO | WO 2004/056581 | 7/2004 |
| WO | WO2004/081475 | 9/2004 |
| WO | WO2004078477 A1 | 9/2004 |
| WO | WO2004088760 | 10/2004 |
| WO | WO200609958 A1 | 11/2004 |
| WO | WO2005041632 A2 | 5/2005 |
| WO | WO2005043598 A2 | 5/2005 |
| WO | WO2005043954 A2 | 5/2005 |
| WO | WO2005091392 | 9/2005 |
| WO | WO2005094390 A2 | 10/2005 |
| WO | WO2005100961 A2 | 10/2005 |
| WO | WO2005101535 A2 | 10/2005 |
| WO | WO2006072071 A2 | 7/2006 |

OTHER PUBLICATIONS

Final Office Action dated Apr. 17, 2007 from related U.S. Appl. No. 11/109,903, filed Apr. 19, 2005, by Mark Owen, et al.
Taiwan Intellectual Property Office, translation of Examination Report for corresponding Taiwan Patent Application No. 094112503, including Search Report, 4 pages.
"LIA Handbook of Laser Material Processing," 2001, pp. 290, 548.
"Electrically pumped vertical-cavity GaN-based LED shows directional emission," Laser Focus World, Feb. 2002, p. 11.
"Spacing of High-Brightness LEDs on Metal Substrate PCB's for Proper Thermal Performance," James Petroski, IEEE Inter Soc. Conference on Thermal Phenom, 2004.
PCT International Search Report dated Nov. 19, 2003 and International Preliminary Examination Report dated Sep. 29, 2003 for International PCT Application No. PCT/US03/14625, filed May 8, 2003, 6 pages.
PCT International Search Report and Written Opinion dated Jun. 3, 2005 for International PCT Application No. PCT/US04/36260, filed Oct. 28, 2004, 5 pages.

PCT International Search Report and Written Opinion dated Jun. 17, 2005 for International PCT Application No. PCT/US04/36370, filed Nov. 1, 2004, 6 pages.

PCT International Search Report and Written Opinion dated Aug. 26, 2005 for International PCT Application No. PCT/US05/09407, filed Mar. 18, 2005, 11 pages.

Martin, S. et al, LED Applications for Phototonics Adhesive Curing, Proc. of SPIE, Jun. 2002, vol. 4833 pp. 296-303.

Not yet published related U.S. Appl. No. 11/614,753, filed Dec. 21, 2006; Specification and Figures; 58 pages.

PCT International Search Report and PCT Written Opinion dated Oct. 13, 2006 for International PCT Application No. PCT/US05/13448, filed Apr. 19, 2005, 8 pages.

PCT International Search Report and PCT Written Opinion dated Sep. 28, 2006 for International PCT Application No. PCT/US05/11216 filed Mar. 30, 2005, 9 pages.

PCT International Search Report and PCT Written Opinion dated Oct. 16, 2006 for International PCT Application No. PCT/US05/09076 filed Mar. 18, 2005, 10 pages.

Not yet published related U.S. Appl. No. 11/342,363, filed Jan. 26, 2006; Specification and Figures; 44 pages.

Not yet published related U.S. Appl. No. 11/434,544 filed May 12, 2006 Specification and Figures; 28 pages.

PCT International Search Report and Written Opinion dated Jun. 7, 2006 for International Application No. PCT/US04/36046, filed Oct. 29, 2004. 6 pages.

Supplemental European Search Report and written opinion for corresponding EU application No. EP03724539, dated Nov. 21, 2007, 8 pages total.

First Office Action dated Sep. 14, 2006 from related U.S. Appl. No. 11/109,903, filed Apr. 19, 2005, by Mark Owen, et al. 7 pages.

First Office Action dated Nov. 14, 2007 issued after a Final Office Action and Request for Continued Examination for related U.S. Appl. No. 11/109,903, filed Apr. 19, 2005, by Mark Owen, et al. 6 pages.

Applicant Response to First Office Action filed with the United States Patent and Trademark Office on Dec. 13, 2006 for related U.S. Appl. No. 11/109,903, filed Apr. 19, 2005, by Mark Owen, et al. 13 pages.

Applicant Response to Final Office Action filed with the United States Patent and Trademark Office on Aug. 17, 2007 for related U.S. Appl. No. 11/109,903, filed Apr. 19, 2005, by Mark Owen, et al., 14 pages.

* cited by examiner

FIG. 8
① CONTINUOUS AT VARIOUS CURRENT LEVELS (AMPS)
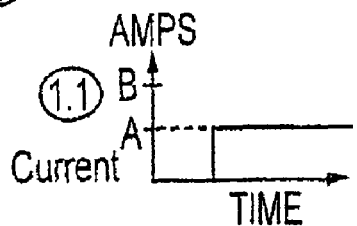
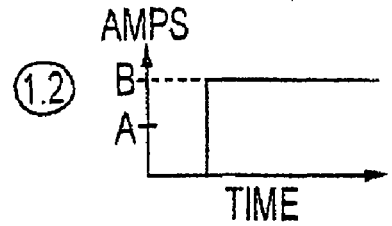
② PULSED USING VARIOUS TIME ON & OFF PERIODS AND/OR CURRENT LEVELS (AMPS)
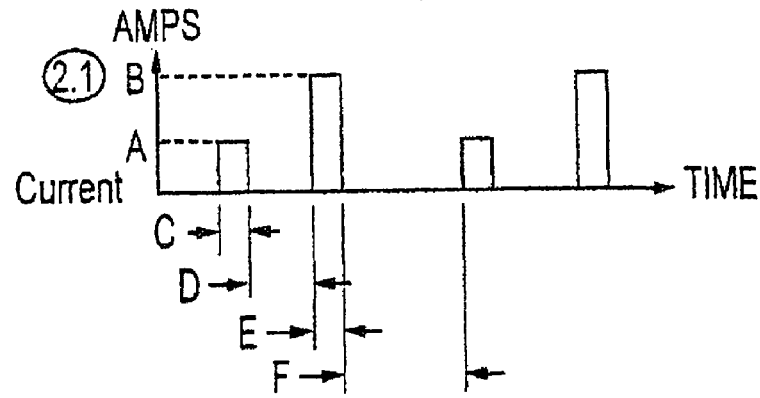
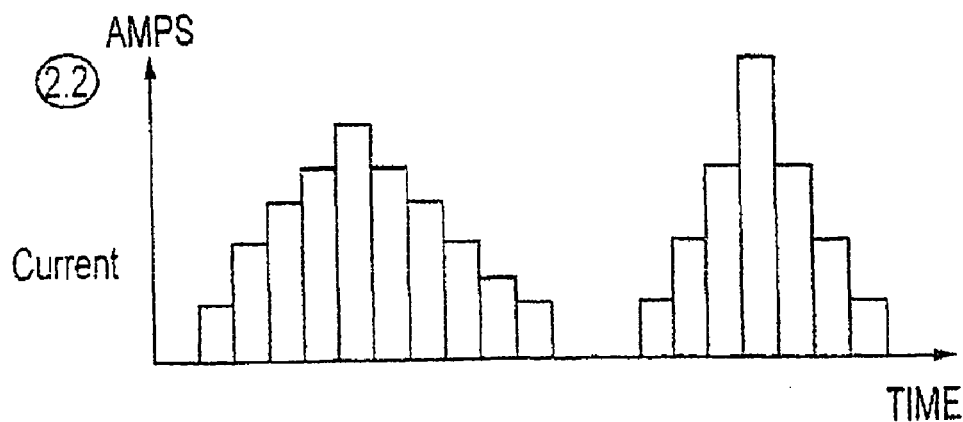

HIGH EFFICIENCY SOLID-STATE LIGHT SOURCE AND METHODS OF USE AND MANUFACTURE

This application is a Continuation-in-Part application claiming the benefit of PCT Application No. PCT/US03/14625 entitled "HIGH EFFICIENCY SOLID-STATE LIGHT SOURCE AND METHODS OF USE AND MANUFACTURE," filed May 8, 2003, the entire disclosure of which is hereby incorporated by reference as if set forth in its entirety for all purposes.

TECHNICAL FIELD

This invention is generally directed to a solid-state light source having an electromagnetic radiation density sufficient to perform a variety of functions in a variety of production applications.

BACKGROUND OF THE INVENTION

High intensity pressure arc lamps of various varieties (for example, metal halide, mercury, Xenon, Excimer, and halogen) and other high-intensity light sources are used in the majority of commercial and industrial applications involving, for example, projection, illumination and displays, inspection, initiation of chemical or biological processes, image reproduction, fluorescence, exposure, sterilization, photopolymer polymerization, irradiation, and cleaning. In each of the applications above, a high irradiation bulb generates a high-intensity broad spectral output of incoherent light that is filtered and spatially modified through the use of complicated optics to allow the emission of a narrow spectral band of light, such as, ultraviolet (UV) light with the proper intensity and spatial properties for the desired application. Unfortunately, conventional high-intensity light sources have a variety of disadvantages, as illustrated in the following examples.

UV light is an effective tool in many production applications in many industries. For example, UV light is used for photopolymer polymerization, a process used widely for various processes such as, printing, lithography, coatings, adhesives, processes used in semiconductor and circuit board manufacturing, publishing, and packaging. UV light, due to its high photon energy, is also useful for molecular excitation, chemical initiation and dissociation processes, including, fluorescence for inspection and measurement tasks, cleaning processes, and sterilization, and medical, chemical, and biological initiation processes, and used in a variety of industries such as, electronics, medicine, and chemical industries. The efficiency and duration of conventional light sources for these applications is extremely low. For instance, 8000 W ultraviolet lamp sources (after filtering) are used in exposure of polymer resists, but they provide only 70 W of power in the spectral range required by the process. Therefore, more efficient semiconductor light sources are needed.

Arrays of semiconductor light sources such as LEDs and laser diodes are more efficient than high pressure light sources and offer advantages over lamps and most other high-intensity light sources. For example, such arrays of semiconductor light sources are four to five times more efficient than that of high-intensity light sources. Other advantages of such semiconductor light source arrays are that they produce a far greater level of spectral purity than high-intensity light sources, they are more safe than high-intensity light sources since voltages and currents associated with such diodes are lower than those associated with high-intensity light sources, and they provide increased power densities since due to smaller packaging requirements. Furthermore, semiconductor light source arrays emit lower levels of electromagnetic interference, are significantly more reliable, and have more stable outputs over time requiring less maintenance, intervention, and replacement than with high-intensity light sources. Arrays of semiconductor light sources can be configured and controlled to allow individual addressability, produce a variety of wavelengths and intensities, and allow for rapid starting and control from pulsing to continuous operation.

None of the prior art discloses a semiconductor light source that can be adapted for a variety of applications and/or provide the high power densities required by a variety of applications.

SUMMARY OF THE INVENTION

The present invention overcomes the problems in the prior art by providing a solid-state light source adapted for a variety of applications requiring relatively high power density output. For example, the present invention may be used in material transformation, projection, and illumination applications. This is achieved by a unique array of solid-state light emitters that are arranged in a dense configuration capable of producing high-intensity power output that prior to this invention required inefficient high-intensity lamps and/or expensive and complex laser devices.

The device of this invention is capable of producing power densities greater than about 50 mW/cm$^2$ for any application requiring such power density. The device of this invention may be used to produce power densities within the range of between about 50 mW/cm$^2$ and 6,000 mW/cm$^2$. The device may be configured differently for a variety of applications each of which may have different requirements such as, optical power output density, wavelength, optics, drive circuitry, and heat transfer. For example, the device may include a drive circuitry to supply power necessary to achieve the density of power output for a particular application. Additionally, the device may include various optics for applications in which a specific light wavelength is required such as, in fluorescent imaging or backside semiconductor wafer inspection.

In one preferred embodiment, the present invention provides a solid-state light module having a thermally conductive substrate with multiple chips of LEDs mounted in a spatially dense arrangement such that illumination is achieved at sufficient intensities to perform physical processes and/or to be utilized in projection and/or illumination applications. The solid-state light source of the present invention can be utilized to perform functions in a variety of applications in such areas of, for example, projection, exposure, curing, sterilization, cleaning, and material ablation. The solid-state light source achieves high efficiency, spectral purity, power densities, and spatial characteristics for each of the applications described above, as well as other applications that require efficient light production.

The present invention provides a solid-state light source that is self-contained, thus eliminating the need for intricate optical coupling mechanisms required by many prior art devices. Furthermore, the solid-state light source of the present invention optimizes light output and is advantageous in the design of small cost effective LED projector systems.

The foregoing embodiments and features are for illustrative purposes and are not intended to be limiting, persons skilled in the art being capable of appreciating other embodiments from the scope and spirit of the foregoing teachings.

BRIEF DESCRIPTION OF THE DRAWINGS

FIGS. 8 and 9 are graphic illustrations of various light waveforms for a variety of applications.

DETAILED DESCRIPTION OF THE INVENTION

Figure 1:
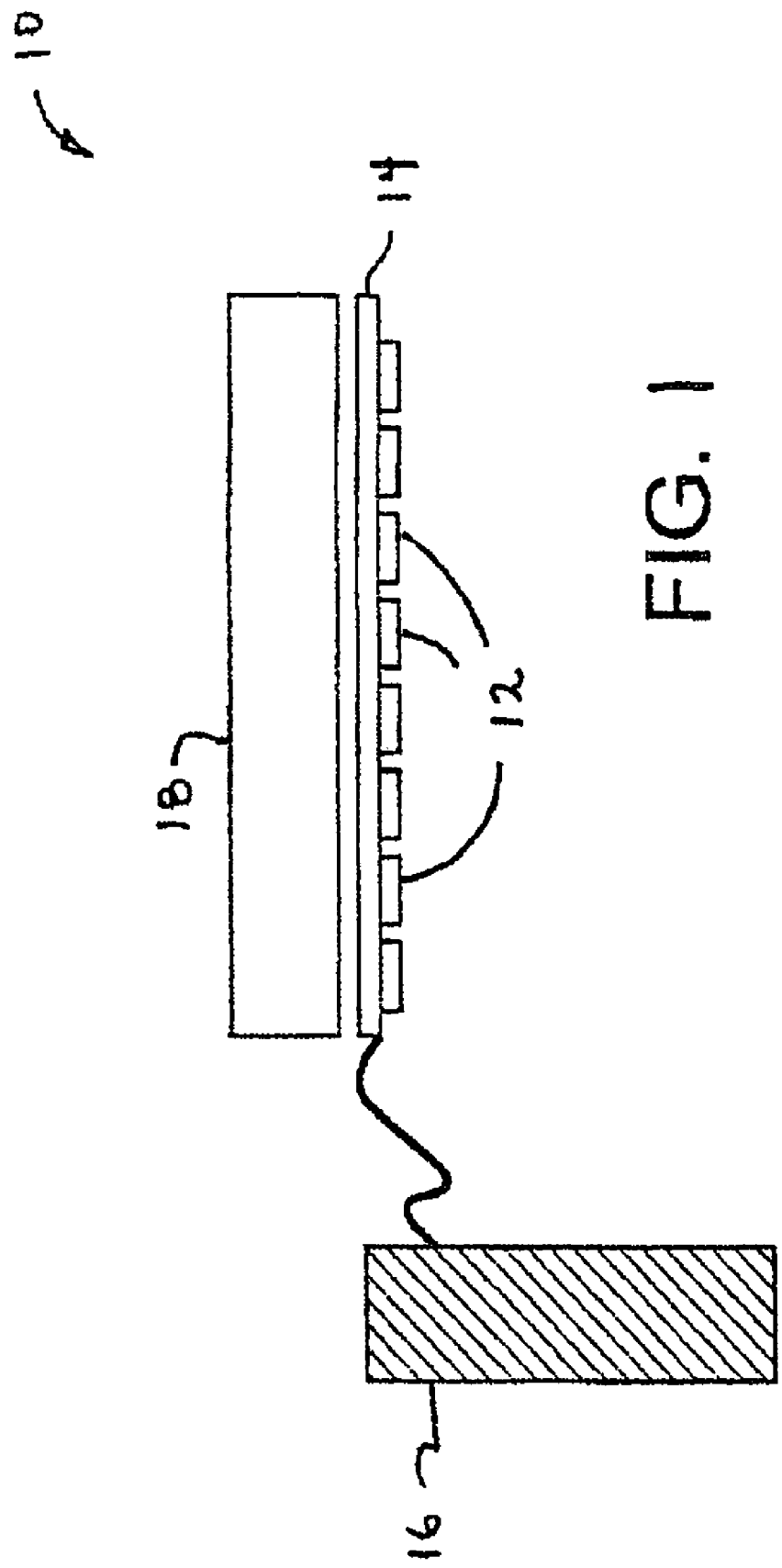
FIG. 1 shows a schematic view of a basic solid-state light module of the present invention.

The present invention provides a lighting module that serves as a solid-state light source capable of performing operations in a variety of applications requiring high density power output. The device of the present invention includes a dense chip-on-board array of solid-state light emitters that produce high-intensity power output and further includes heat transfer; drive circuitry, light intensity, spectral purity, spatial uniformity, and directionality required for a variety of applications. Such applications are typically those requiring a power density output of over about 50 mW/cm$^2$. Most applications typically require between about 50 mW/cm$^2$ and 6,000 mW/cm$^2$ and the present invention can provide power output in this range. However, it is contemplated that the lighting module of the present invention may be utilized in applications requiring a power density output greater than about 6,000 mW/cm$^2$ Applications requiring power density output of between about 50 mW/cm$^2$ and 6,000 mW/cm$^2$ include the following:

projection applications that provide illumination for inspection operations, and for displays and projectors that project and control light;

imaging applications such as, lithography, printing, film, and image reproductions, and other applications that transfer images; and material transformation applications, such as, initiating chemical or biological processes, photopolymerization (including curing of coatings, adhesives, inks, and lithographic exposure of photopolymers to create a pattern), cleaning, sterilization, ionization, and ablation (material removal with light).

The lighting module of the present invention includes an array of solid-state light emitters that may be configured to produce the required light intensity for each application of use. As used herein, the phrase "solid-state light emitter" means any device that converts electric energy into electromagnetic radiation through the recombination of holes and electrons. Examples of solid-state light emitters include semiconductor light emitting diodes (LEDs), semiconductor laser diodes, vertical cavity surface emitting lasers (VCSELs), polymer light emitting diodes, and electro-luminescent devices (i.e., devices that convert electric energy to light by a solid phosphor subjected to an alternating electric field). In the following description, LEDs are used to illustrate solid-state light emitters.

LEDs are arranged in a dense array on a substrate, as discussed below. The density of the chip array or, in other words, the spacing of the chips on the substrate, may vary according to the application of intended use. Each application of intended use may require a different power density output that may be achieved based on the spacing (or density) of the chips on the substrate, depending on the power of chip used. Additionally, each application may require different light wavelengths or a mixture of wavelengths for the application. Table 1 below shows examples of power density outputs that can be achieved by various chip array densities or spacing using 12 mW and 16 mW chips. For example, an array of 12 mW chips formed on a substrate in a density of 494 chips/cm$^2$ (22 chips/cm) produces a power density output of 5037 mW/cm$^2$. This power output density may be required for cleaning applications using light wavelengths of between 300-400 nm. For cleaning applications requiring a higher power density output, an array of 16 mW chips formed in the same density described above produces a power density output of 6716 mW/cm$^2$. While individually packaged prior art semiconductors like LEDs, VCSELs, and laser diodes are typically arranged on 4mm or larger center-to-center pitches, this invention achieves significant increases in power density by arranging the devices on center-to-center pitches below 3 mm, and more typically between 1 mm and 2 mm center-to-center pitches. In view of the teachings herein, it should be apparent to one skilled in the art that other power densities other wavelengths, and other device spacings are possible limited only by the future availability of devices. As defined herein, a dense array of solid state emitters is one a plurality of solid state emitters are arranged in an array of 3 mm or less center-to-center spacing to provide a power density output of at least 50 mW/cm$^2$.

TABLE 1

| Power density (mW/cm$^2$) as a function of chip spacing and chip power | | | | | | | | | | | |
|---|---|---|---|---|---|---|---|---|---|---|---|
| Micron Pitch | 450 | 650 | 850 | 1050 | 1250 | 1450 | 1650 | 1850 | 2050 | 2250 | 2450 | 2650 |
| mm Pitch | 0.45 | 0.65 | .085 | 1.05 | 1.25 | 1.45 | 1.65 | 1.85 | 2.05 | 2.25 | 2.45 | 2.65 |
| Number of chips per cm | 22 | 15.4 | 11.8 | 9.5 | 8.0 | 6.9 | 6.1 | 5.4 | 4.9 | 4.4 | 4.1 | 3.8 |
| Number of chips per sqr cm | 494 | 237 | 138 | 91 | 64 | 48 | 37 | 29 | 24 | 20 | 17 | 14 |
| mW/cm2 using 12 mW chips | 5037 | 2414 | 1412 | 925 | 653 | 485 | 375 | 298 | 243 | 201 | 170 | 145 |
| mW/cm2 using 16 mW chips | 6716 | 3219 | 1882 | 1234 | 870 | 647 | 500 | 397 | 324 | 269 | 227 | 194 |

FIG. 1 illustrates the basic construction of the solid-state lighting module 10 of the present invention in which a plurality of solid-state light emitters such as, LED chips 12 are mounted in a dense array on a substrate 14. A variety of LED chips are commercially available across a spectral range of visible and invisible light and a person skilled in the art may select an LED chip depending on the application of intended use. One example of a suitable LED chip for a material transformation applications such as, curing, is P/N C395-XB290-E0400-X, manufactured by Cree, Inc., located in Durham, N.C. Module 10 is connected to a power source 16 to power LED chips 12 that produce light output of an intensity to perform a desired operation. The spacing or density of LED chips 12 on substrate 14 is determined by the power density output requirements of the desired operation. For example, from Table 1 above it can be seen that to obtain a power density output of 2412 mW/cm$^2$ LED chips 12 must be mounted on substrate 14 in an array having a density of 237 LED chips/cm$^2$. For thermal control, substrate 14 is preferably mounted on a heat sink 18. Substrate 14 may be made of a variety of materials as will be described below. Heat sink made of any thermally conductive material such as, aluminum brass, copper, alloys or many other materials designed to efficiently conduct heat. As described herein, individual LED chips are surface mounted to the substrate. However, multiple LED arrays may be provided as a single integrated circuit die. Larger LED arrays may be assembled by arranging several of the die into a hybrid circuit array.

Figure 2:
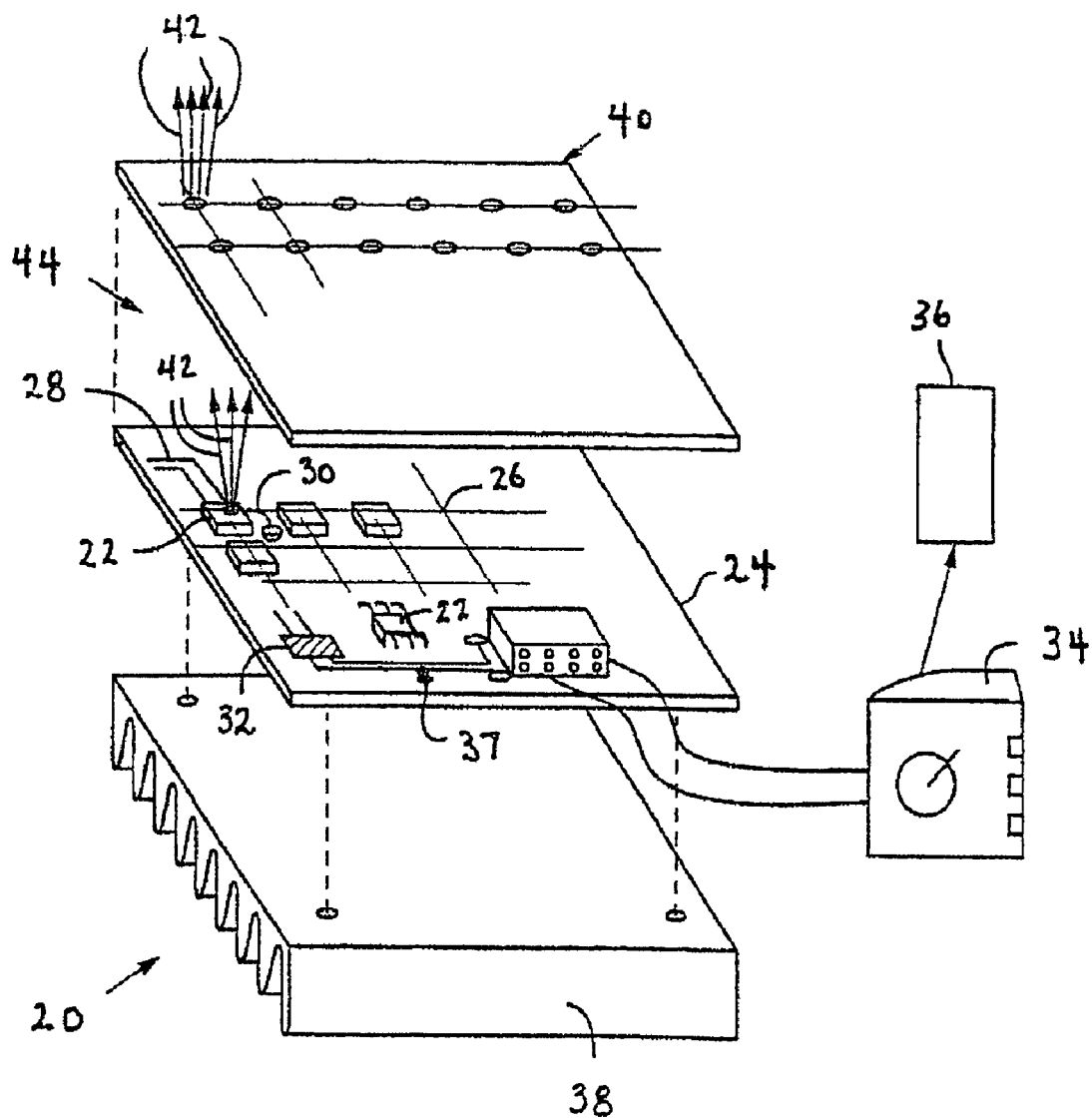
FIG. 2 shows an exploded view of one embodiment of the solid-state light device.

FIG. 2 further illustrates one possible example of a solid-state lighting module 20 capable of producing a power density output that may be used in a material transformation processes. Module 20 includes plural solid-state light emitters such as, LED chips 22 mounted on substrate 24 in a dense array 26 to produce a high density power output to perform a material transformation process. LED chips that produce a wavelength capable of performing a material transformation process at a power density output of greater than 50 mW/cm$^2$ are commercially available. One skilled in the art may select a LED chip depending on its wavelength output for a specific material transformation application. As discussed above, the spacing or density of LED chips 22 depends of the power density output requirement of the material transformation process. Substrate 24 serves as an electrical insulator and a thermal conductor and can be made of ceramic material such as, Alumina ($Al_2O_3$), Aluminum Nitride (AlN), sapphire, Silicon Carbide (SiC), diamond, or Beryllium Oxide (BeO); dielectric coated metal like aluminum copper or other alloys, semiconductor materials such as, GaAs or Si; or laminate-based or other substrates that use thermal vias or metal layers to conduct heat. These materials are thermally transmissive for the purposes of this invention. Hereinafter, a thermally transmissive substrate is one made of any one of these materials. Conductive circuitry patterns 28 are formed on one surface of substrate 24 and are formed of electrically conductive materials such as, copper, palladium, gold, silver, aluminum, or alloys or layers thereof. LED chips 22 are mounted on substrate 24 by solder, conductive adhesives, eutectic bonding, or other known metal bonding techniques and are electrically connected to circuitry patterns 28 by appropriate conductive leads, such as wires 30. Alternatively, LED chips 22 may be formed directly on substrate 24.

Wires 30 are connected to LED chips 22 and substrate 24 through circuitry patterns 28 by any wire bonding or electrical joining technique, including wire bonding, flip chip, surface mount, or other bonding technique. Circuitry patterns 28 may include connections to thick or thin film passive components 32. Thick film components 32 can be laser trimmed to achieve uniform light intensities across array 26. A power supply 34 is provided and is connected to circuitry patterns 28 to power LED chips 22. Power supply 34 may be connected to or controlled by a computer controller 36 so that LED chips 22 can be turned on, off, or pulsed for variable times or intensities. At least one temperature sensor 37 may be connected to circuitry patterns 28 in any known manner to monitor the temperature of substrate 24. Sensor 37 may be connected through control circuitry to power supply to prevent the module 20 from overheating. Thus, input from temperature sensors 37 may be used to provide real-time in-situ temperature control. Thermal stability and heat dissipation may be achieved, if desired, by mounting substrate 24 onto a heat sink 38. This heat sink can be comprised of heat conductive materials like copper or aluminum, heat pipes consisting of a metal cylinder containing a fluid for enhanced heat convection, or a water-cooled heat conducting material.

Optical properties of spatial directionality, uniformity and spectral filtering may be achieved, if desired, by an optical component 40, which might include a micro lens array of refractive or diffractive components or other optical redirection technology, as well as spectral filtering. Light output 42 from LED chips 22 can be focused, collimated, and/or made more uniform. Although not required, optical efficiency may be achieved by matching the index of refraction of a gas, liquid, or transparent polymer hermetically sealed in a gap or space 44 created between the substrate 24 and optical component 40 for maximum reliability. Suitable refracting gases are known to persons skilled in the art and may include helium, nitrogen, argon, or air. Suitable refracting liquid could include coolants or optical mineral oils. Suitable transparent polymers include optical gels of silicone and epoxy, and rigid polymers of acrylic, polycarbonate, epoxy and others known to persons skilled in the art. The gas, liquid or polymer may further improve thermal dissipation. Optical efficiency can also be improved by addition of reflective surface coatings on substrate 24 or by the addition of known thin film coatings on optical component 40 or component 22.

Figure 3:
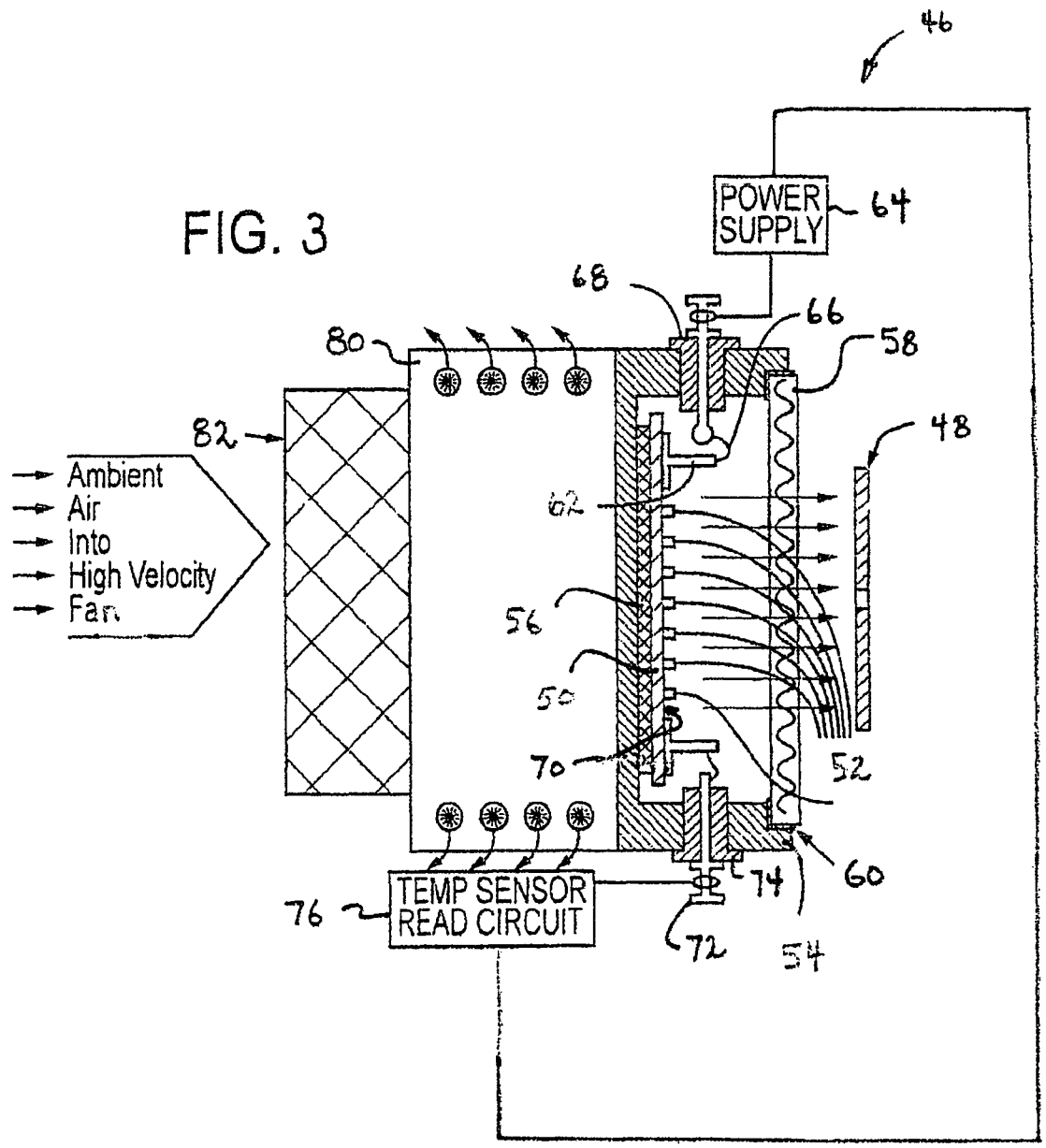
FIG. 3 is a cross sectional view of another embodiment of the solid-state light device.

One possible example of a solid-state light device 46 is seen in FIG. 3 capable of curing the coatings on work object 48 such as, a CD/DVD device with a sealed, air cooled, LED chip array. In order to perform a curing operation, device 46 may provide a power output density of about 30-6000 mW/cm$^2$ of light of a wavelength of between about 300-400 nm. Device 46 includes a substrate 50 made of any material as discussed above but is preferably made of ceramic or alumina. An array of LED chips 52 is disposed on substrate 50 so as to produce a light pattern slightly larger than work object 48. This larger pattern ensures proper edge cure down the sides of work object 48. Substrate 50 may be mounted within a module housing 54. Alternatively, a carrier can be added for ease of manufacturing and service. The carrier uses the permanent bonding agent 56 to attach substrate 50 and a non-permanent thermally conductive grease between the carrier and the housing 54. The carrier is then attached mechanically to the housing 54. A permanent bonding agent 56 such as conductive adhesives, paste, or other adhesive that conducts heat may be used to mount substrate 50 in housing 54. Housing 54 may be made of a metal that is easy to machine and is an excellent thermal conductor for heat dissipation. A window 58 of glass or plastic is formed in module housing 54 to allow light produced by LED chips 52 to pass through to work object 48. Window 58 is sealed to module housing 54 by a high light transmission environmental seal 60 which may be any commercially available bonding seal. A terminal 62 is attached to or formed on substrate 50 and is connected to a power supply 64 through a stress relief electric connection 66 mounted in an electrical insulator 68 in module housing 54. An optional temperature sensor 70 is also provided on substrate 50 and is connected through a terminal 72 and insulator 74 to a temperature sensor read circuit 76. Temperature sensor read circuit 76 is connected to power supply 64 to prevent LED chips 52 from overheating. Typically, the temperature threshold is about 80° C. Module housing 54 is mounted by any connector such as, screws (not shown) on a heat sink 80. Heat sink 80 may have a plurality of fins made of any thermally conductive material such as, aluminum. A fan 82 may be connected to heat sink 80 so that fan 82 takes in ambient air and blows it through heat sink 80. Heated air is then transported away from module 46. Many curing applications are performed with light wavelengths of about 395 nm. LED chips 52 preferably produce light output in a range corresponding to that which activates a curing agent in the curing application of intended use. LED chips 52 may be pulsed to increase their output intensity to achieve a power output density of greater than 400 mW/cm$^2$ for a particular curing application. However, other curing applications may require other light wavelengths and other power density outputs.

Figure 4:
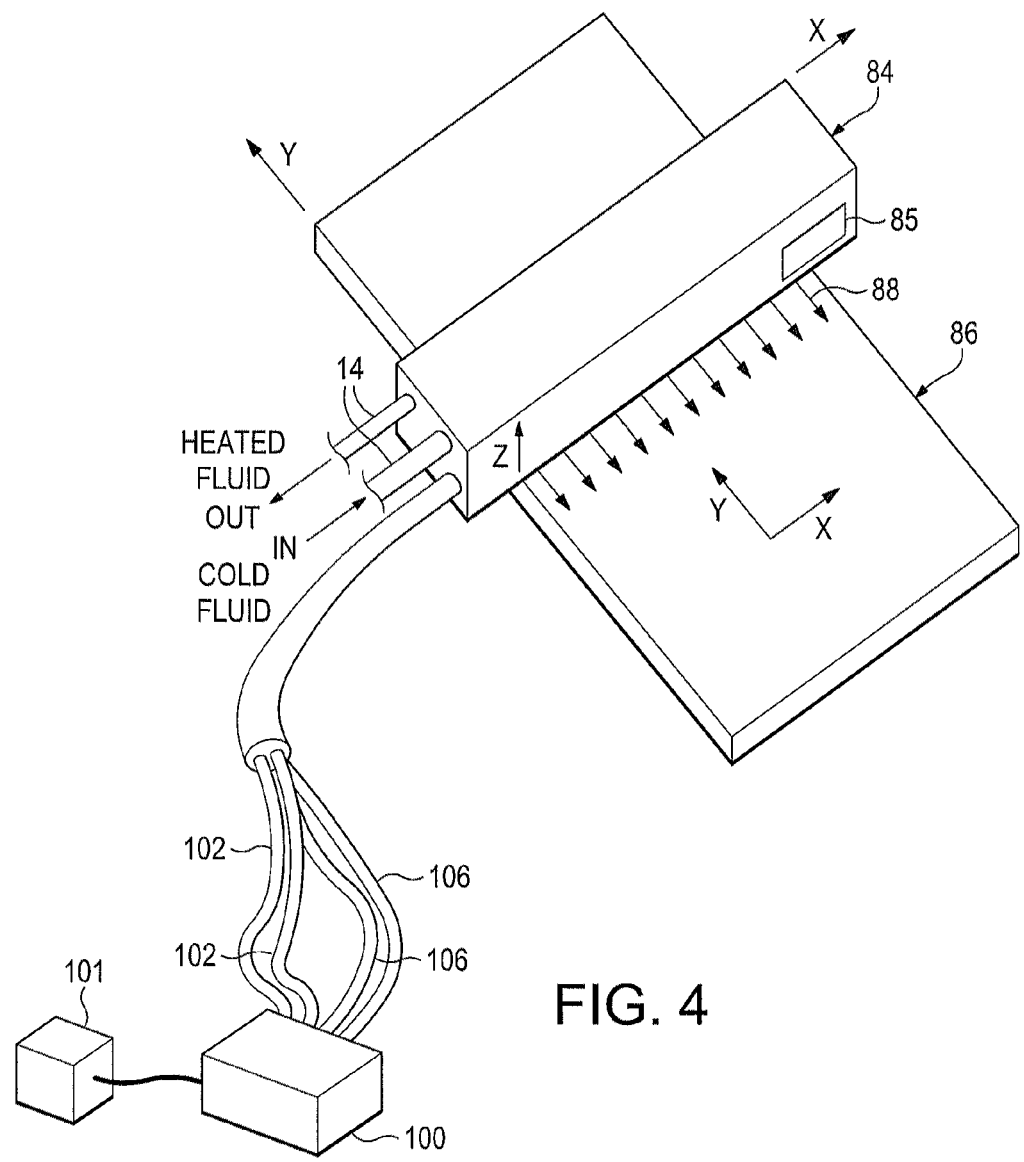
FIG. 4 is a perspective view of a solid-state light bar.
Figure 5:
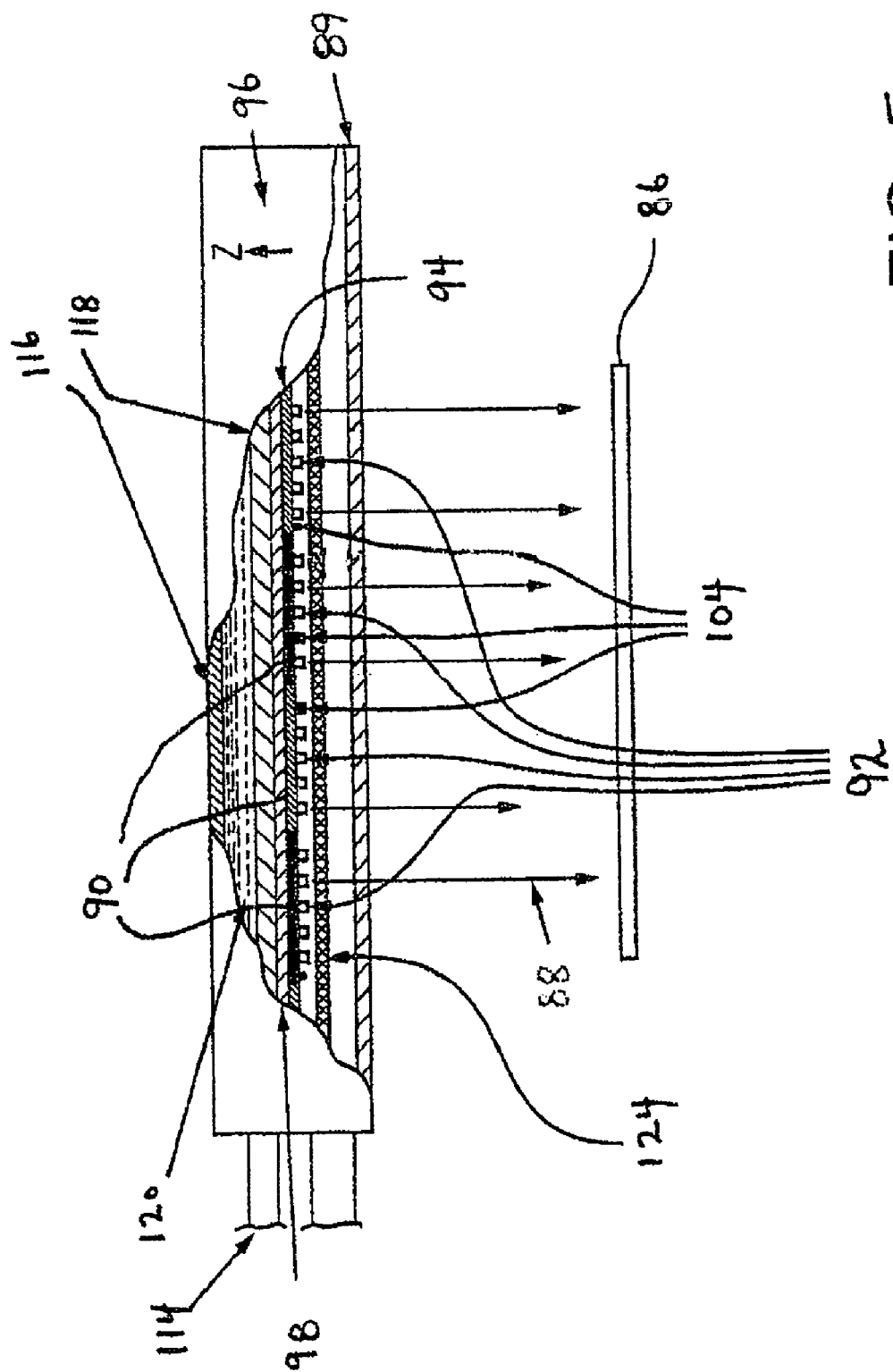
FIG. 5 is a partial cross sectional view of the solid-state light bar of FIG. 4.
Figure 6:
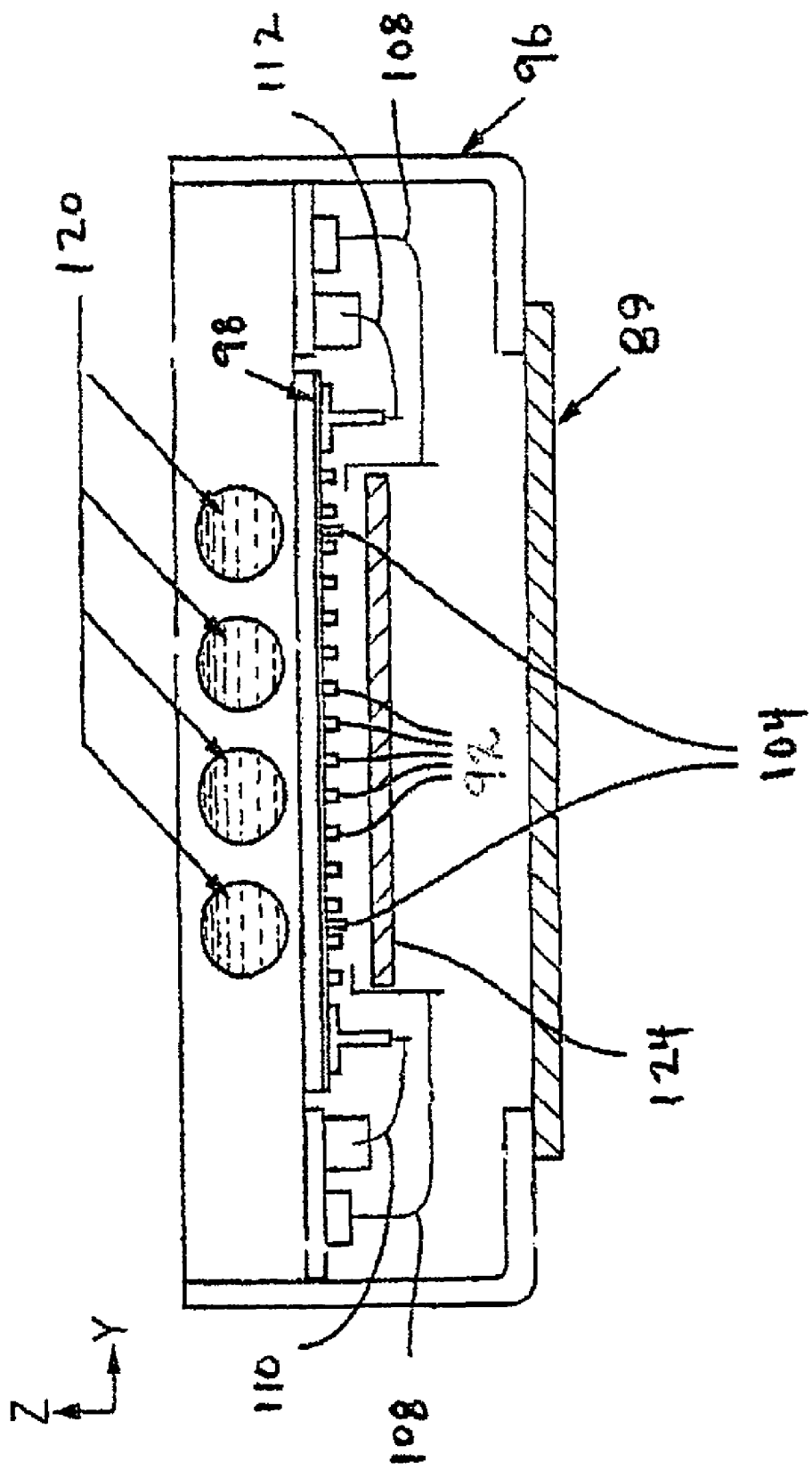
FIG. 6 is a cross sectional end view of the solid-state light bar of FIG. 4.

FIGS. 4-6 show an embodiment that incorporates multiple solid-state light modules into a light bar 84 for in-line material transformation applications such as, high-intensity surface modification such as ink or coating curing or image exposure applications. For example, Low Viscosity Ultraviolet Curing Ink manufactured by International Ink Co. of Gainsville, Ga., reacts at around 200 mW/cm$^2$ using a wavelength of between about 350 and 450 nm. Light bar 84 includes multiple modules arranged in a line or an array and extends along an axis X. Light bar 84 is preferably moved relative to a target or work object along an axis Y allowing light output 88 to perform a process on work object 86. Light uniformity is improved by moving light bar 84 relative to work object 86 because the movement spread light output 88 evenly across work object 86 along the Y-axis. To improve uniformity along the X-axis, light bar 84 may also be moved along the X-axis to spread light output 86 along that axis. Light output 88 may be averaged by moving light bar 84 along both the X and Y axes such as, by vibration. Additionally, a light averaging optical element, such as a diffuser (not shown), may be incorporated in light bar 84. Furthermore, solid-state light modules may be angled so that the witness line of their joining is not evident in work object 86. Light bar 84 may be of various configurations and can be moved by any motive means necessary such as 85 to achieve the objectives of the process for which it is to be used.

As seen in FIGS. 5 and 6, light bar 84 includes multiple solid-state light modules 90 mounted thereon. Each module 90 includes a dense array of LED chips 92 mounted on a substrate 94. LED chips 92 are surface mounted and wire bonded to substrate 90 in a high density array according to the power density output of the operation. Each substrate 94 is preferably a printed circuit board with optimum heat transfer materials, as described above. Substrates 94 may be mounted to a light bar housing 96 through a bonding agent 98, preferably having good thermal conductivity. Alternatively, the substrate 94 can be mounted to removable carriers for ease of manufacturing. The carriers attach to substrates 94 with permanent, thermally conductive bonding agent 98. The carriers are mechanically attached to the light bar housing 96. The carrier completes the module 90 including the substrate and other components. Modules 90 are mounted in a manner so that light output 88 produced by LED chips 92 is directed toward work object 86 through a window 89. Alternatively a copper tube may be pressed into or attached by a bonding agent 98 or similar agent. The copper tube contains the fluid flow, simplifies construction and lowers cost of Module 90. In this embodiment the housing 96 is one part. A power supply 100 (FIG. 4) provides power through a first set of cables 102 to power either all modules 90 in light bar 84 or power each module 90 separately. Each substrate 94 may include a temperature sensor 104. Power supply 100 senses the temperature of each substrate 94 through a second set of cables 106. The first and second cable sets 102 and 106 are shown simplified. Preferably, each module 90 will have its own set of power cables so that each module 90 can be controlled separately. Each temperature sensor 104 is connected to a temperature sensing circuit 108 connected to power supply 100. A power in bus bar 110 and a power out bus bar 112 serve as the power input and output connections for light bar 84.

To control the temperature of light bar 84, a fluid tube 114 introduces cooling fluid (coolant) in and carries heated fluid out. Light bar housing 96 includes upper and lower metal plates 116 and 118 such as, aluminum or copper, between which fluid tube 114 is positioned so that heat is transferred from light bar housing 96 to the fluid which is then carried out of light bar housing 96. Alternatively, light bar housing 96 may be provided with plural channels 120 (FIG. 6) through which coolant is supplied by a first hose (not shown) so that the coolant is in direct contact with light bar housing 96 and flows out of light bar housing 96 through a second hose (not shown). This allows for turbulent flow of the coolant, providing greater heat transfer. Power supply 101 (FIG. 4) controls the coolant by sensing the temperature and allowable light output. A separate fan cooled radiator or different means of cooling is applied to remove heat. Light bar 84 is preferably a closed assembly to protect modules 90 from environmental damage including but not limited to physical impact and airborne contaminants, either in gas or liquid phase. A rigid cover 122 provides structural strength and holds window 89 which may be coated for improved UV light transmission, if desired. As seen in FIG. 6, at least one optical element 124 may be provided adjacent to the LED chips 92 to align light output 88 to the Z axis. Optical element 124 may be single or multiple elements and may be separated for each LED chip 92 or be designed to work for several or many LED chips 92. Side reflectors may be used to direct light toward the target. Side reflectors would be located along the sides of the modules 90 or may be incorporated into the said modules 90.

Other material transformation processes may include, resist exposure for circuit boards that include at least one material that reacts to light wavelengths between about 350-425 nm with the optimal wavelength being 365 nm at a power density output of greater than 100 mW/cm$^2$. The substrate may be ceramic such as alumina or Aluminum Nitride (AlN) or any of the other thermally conductive substrates mentioned herein using a fluid cooled heat sink. A collimating optic micro array may be utilized to collimate light output. The LED chips such as those manufactured by Cree, Inc. as discussed above, may be either be pulsed or driven continuously to obtain a power output density of greater than 700 mW/cm$^2$. For some cleaning operations, light wavelengths of between 300-400 nm may be used as some organic materials can be removed using such a range of wavelengths. For example, fingerprints may be removed from a semiconductor wafer using a wavelength of about 365 nm and pulsing the LED chips at less than 100 nsec pulses to obtain a power output density of greater than 5,000 mW/cm$^2$.

Figure 7:
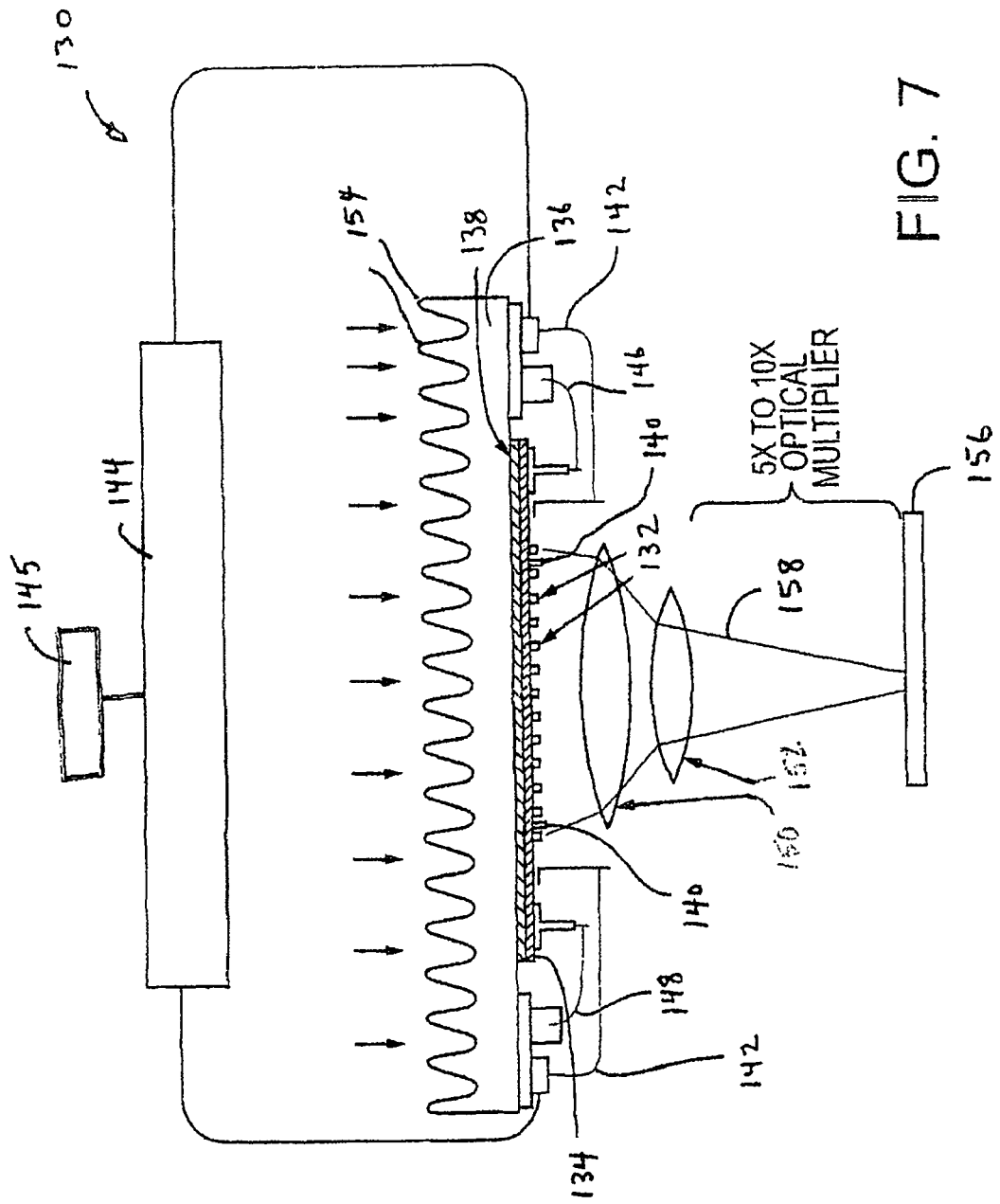
FIG. 7 is a cross sectional end view of another embodiment of a solid-state light device of the present invention.

FIG. 7 shows a solid-state light device 130 wherein optical multiplication of the intensity of the light source is achieved for applications such as semiconductor wafer inspection or fluorescent inspection where a higher intensity of a single wavelength is required. A dense array of LED chips 132 are surface mounted on a substrate 134 having optimum heat transfer properties as discussed above. LED chips that produce a wavelength capable of performing an inspections process at a power density output of greater than 50 mW/cm$^2$ are commercially available. One skilled in the art may select a LED chip depending on its wavelength output for a specific inspection application. Substrate 134 is mounted to a heat sink 136 through a bonding agent 138. Temperature sensors 140 may be provided on substrate 134 and are connected to temperature sensor circuits 142 and are connected to a computer controlled power supply 144 for operation, as discussed above. Power supply 144 with thermal sensing circuitry is controlled by a computer 145 and is connected to substrate 134 through power in bus bar 146 and power out bus bar 148. Heat sink 136 can be any possible configuration to effectively remove heat and is shown with a plurality of fins 154 to dissipate heat. Either ambient air or an air flow provided by a fan (not shown) flows over heat sink fins 154 to cool device 130. Although an air heat sink is shown, it is contemplated that device 130 could also have a fluid tube to carry coolant into and take heated fluid out of the heat sink 136 as shown and described in FIGS. 4-6. Additionally, heat sink 136 could also be a heat pipe or thermal electric cooler. Optical elements 150 and 152 may be provided between LED chips 132 and a work object 156 to focus light 158 to obtain the desired intensity required for the application. For example, optical elements 150 and 152 may increase the light intensity up to between 5 and 10 times. Optical elements 150 and 152 may be any known focusing lens or intensifying optic.

Figure 9:
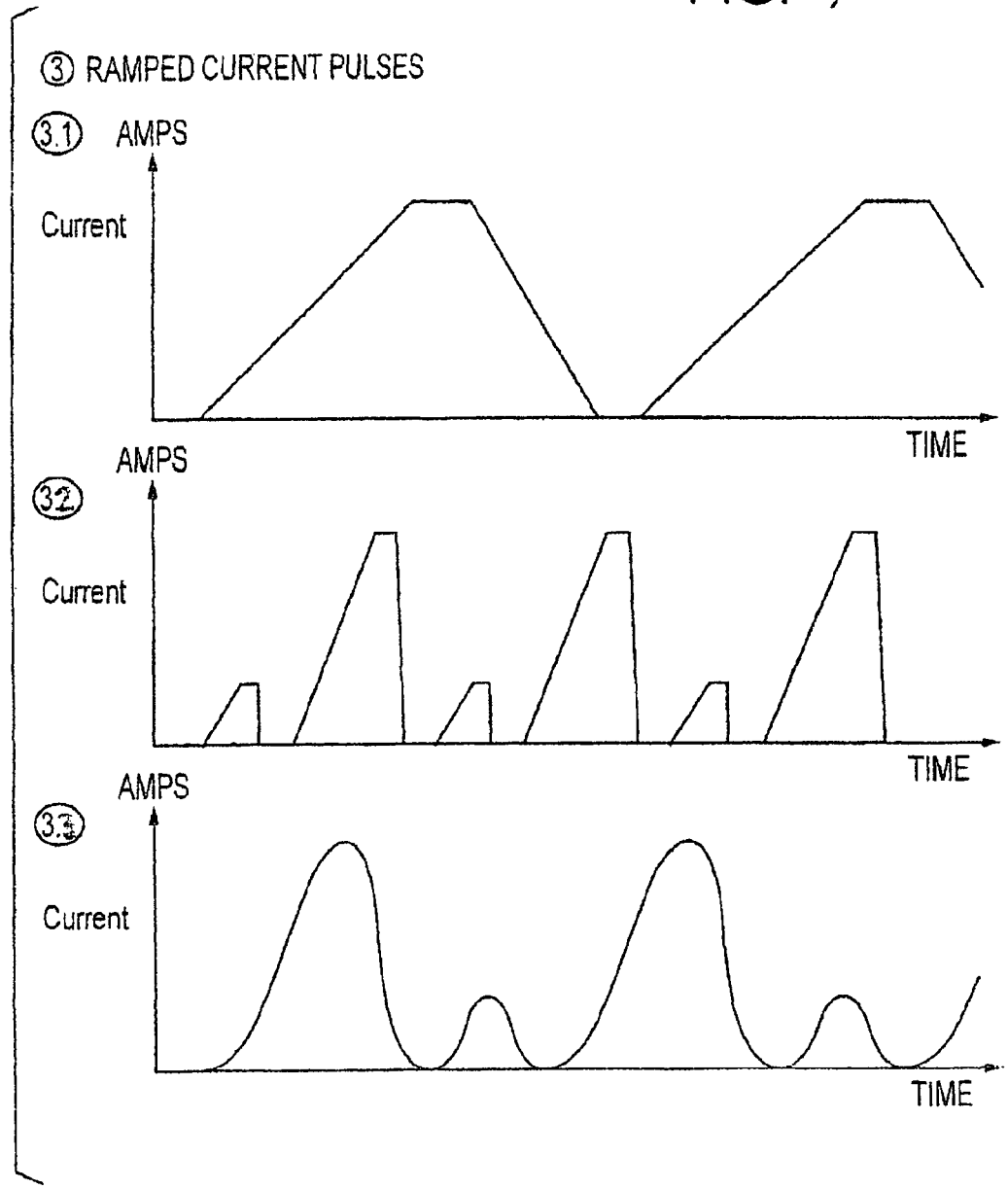

Power supply 144, as well as other power supplies described above, can provide a variety of power waveforms, as seen in FIG. 8, for different applications. For example, power supply 144 may supply constant voltage continuously at various current levels (amps) as seen in the graphical illustrations labeled 1.1 and 1.2 for applications such as, backside wafer inspection and resist exposure for circuit boards. Power supply 144 can also provide pulsed power waveforms using various time on and off periods represented at C, D, E, and F, and/or current levels (amps) as seen in graphical illustrations labeled 2.1 and 2.2 for applications such as, fluorescent inspection, curing for coating for CD ROMS, and cleaning. As seen in FIG. 9, various ramped current pulses are seen in the graphical illustrations labeled 3.1, 3.2, and 3.3 for applications such as, lithography systems and cleaning. LED chips 132 may be pulsed at various frequencies for pulse times as low as 50 nsecs in order to accomplish a specific function. For material processing applications where maximum intensity is required, solid-state light devices like LEDs can be super pulsed, for example, at currents 3 to 5 times their nominal current, or even significantly higher for short periods to achieve a higher intensity. Pulse ramp shapes allow more reliability by not overly stressing the solid-state light devices beyond what the application requires. Additionally, for material transformations where the physical process takes a period of time, the duration of the pulse can be matched to the process requirements. Additionally, for material transformations which are intolerant to heat, the duration and spacing of pulses can be matched to the process requirements.

Figure 10:
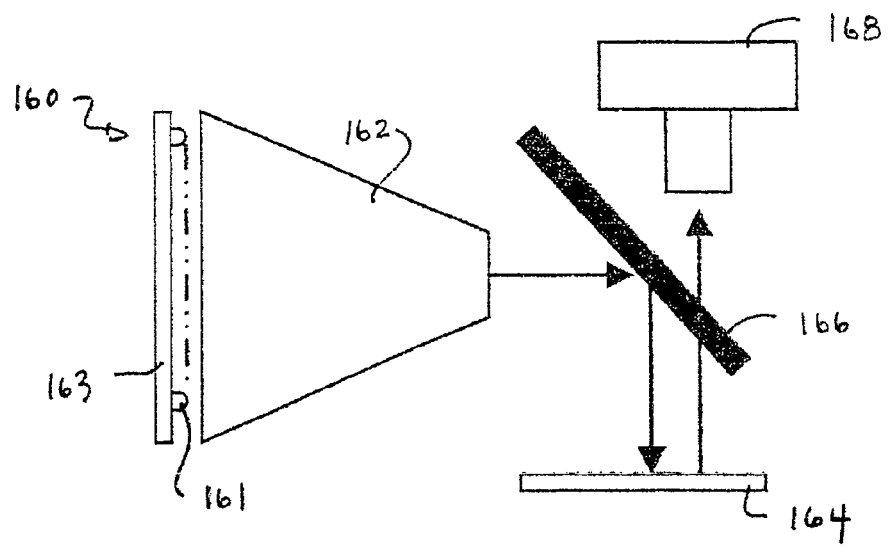
FIG. 10 is a schematic view of an embodiment for increasing the intensity of light output from a solid-state light module.
Figure 11:
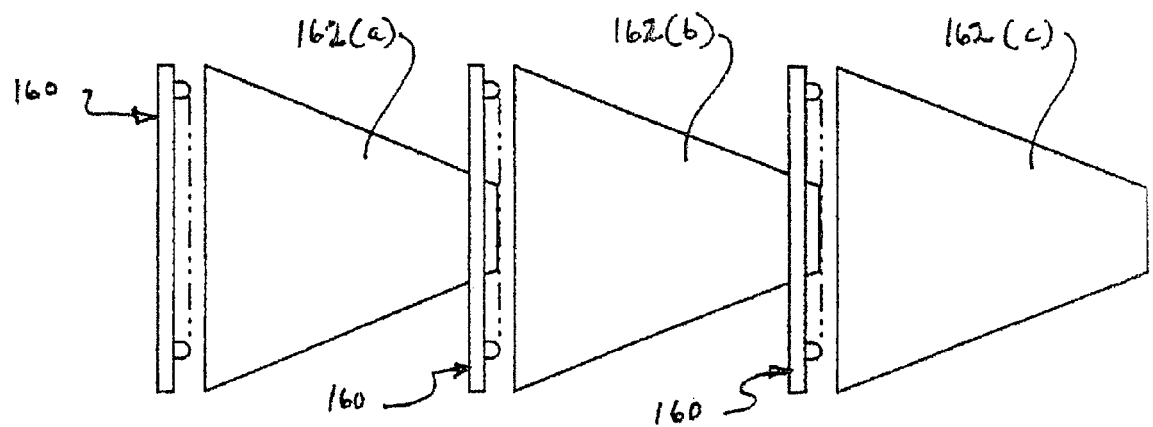
FIG. 11 is a schematic view of another embodiment of FIG. 10 utilizing plural optical elements to increase the intensity of light output.

FIG. 10 illustrates another embodiment of a high-intensity light source that utilizes a reflective/transmissive optical element for inspection applications requiring power density output on greater than 50 mW/cm$^2$. Light from a module 160 is condensed with a first optical device 162 such as, a fused taper, telescopic lens pair, or other optical elements. Module 160 includes a dense array of LED chips 161 surface mounted on a substrate 163. Light is then directed to a work object 164 through a second optical element 166 such as a reflective surface. For fluorescent inspection, module 160 preferably produces light having a wavelength of between 300-400 nm. Second optical element 166 is preferably a highly reflective mirror that reflects greater than 95% at the light wavelength of about 380 nm and highly transmissive at the fluorescent wavelengths between 450-600 nm. Fluorescent wavelengths from work object 164 are transmitted through second optical element 166 to a camera 168 that detects the fluorescent wavelengths. The simplified optics and higher density light output of this embodiment enables applications not possible with prior art inspections devices due to their complicated design and limited uniformity and power density. The embodiments of FIGS. 10 and 11 provide increased light intensity to perform, for example, cleaning, sterilization, and other high power density applications. For example, by feeding 1 W/cm$^2$ coherent power into one or more optical devices 162 to form a 1 mm$^2$ or 4 mm$^2$ beam power density could be increased 100 times, ignoring optical losses. To further increase power density, diode lasers devices in an array could be used instead.

For backside inspection of silicon wafers or for MEMs seal inspections, module 160 preferably includes 1050-2500 nm LED chips or laser diodes having a combined output power density greater than 50 mW/cm$^2$. Second optical element 166 is preferably a 50% beam splitter at the same wavelength as the light output from module 160, which is typically between 1100-1300 nm. This arrangement is effective for work objects 164 that are transmissive at 1100-1300 nm so that the wavelengths transmitted from work object 164 are propagated through second optical element 166 to camera 168 that is sensitive in the near infrared at the source wavelength.

Figure 12:
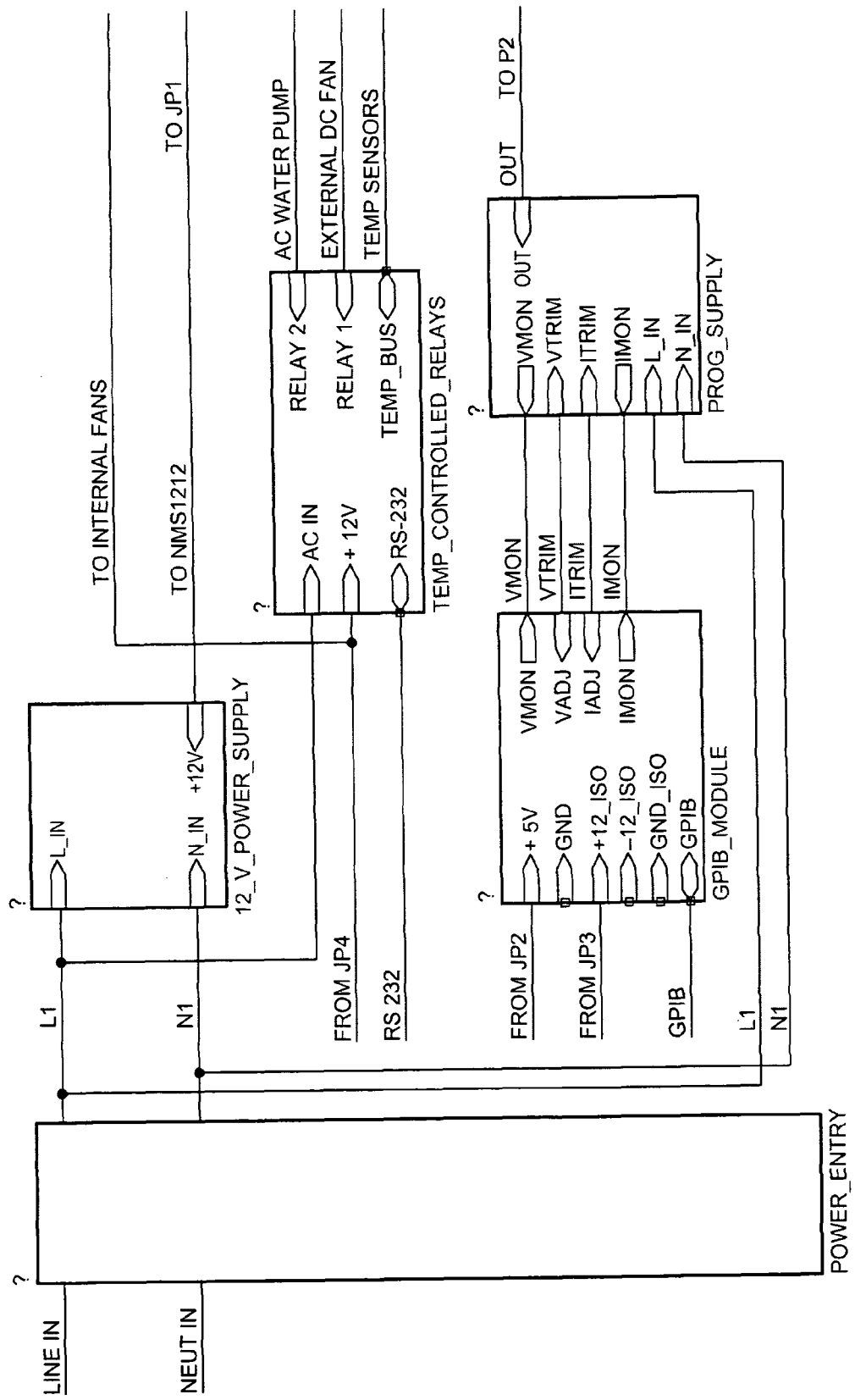
FIG. 12 is a schematic of a power supply for driving the embodiment of FIG. 7.

Light output may be further extended by stacking modules 160 as seen in FIG. 11 in series or optically in parallel. For example, 80% efficiency may be achieved by surface mounting 1,000 1.8 mW LED chips at 1200 nm on substrate 163 in module 162(a); surface mounting 800 similar LED chips of substrate 163 of modules 162(b) and 162(c). This provides a potential of 1.44 W with one module, 2.59 W with two modules, and 3.7 W with three modules. FIG. 12 illustrates a power supply capable of achieving the pulsing and control requirements of the present invention. The programmable power supply shown herein is controlled from a general purpose instrument bus (GPIB) interface circuit board where the output voltage and output current can be remotely programmed and monitored from a computer. The power supply can also be programmed to provide arbitrary output voltage and output current waveforms at various pulse repetition rates and duty cycles sufficient to achieve the functionality detailed in the embodiments.

Figure 13A:
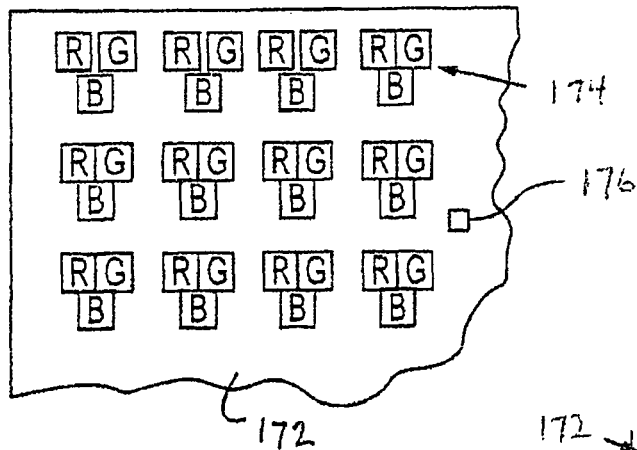
FIGS. 13a and 13b show an embodiment of the present invention which allows full color display or projection of a color image by having individually addressable red, green, blue, or other color emitters.
Figure 13B:
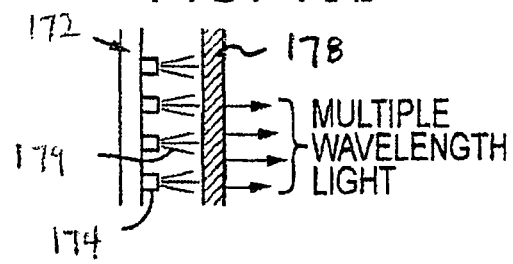

FIGS. 13a and 13b show an embodiment of the present invention that allows spectral mixing by having individually addressable light emitters of predetermined colors. For example, the emitters can be red, green, and/or blue or three different bands in the ultraviolet. The emitters can be arranged in color triads. In addition to standard LED colors, LED chips may be adapted to produce other colors by using colored phosphors or fluorescing coatings or fillers. For example, each LED in earlier described embodiments may be replaced with three LEDs. In other words, one white LED may be replaced with three LEDs of different colors, R,G,B with each separate LED having separate power coming in so that the drive circuitry would allow them to be pulsed as separate colors. White-light LEDs using phosphor coatings are commercially available.

Grounds for a triad of LEDs or other multiple grouping can either be separate or one single common ground. A solid-state light module 170 is partially seen in FIG. 13 in which a thermally conductive substrate 172 includes an array of R, G, B (Red, Green, Blue) LED chips 174 mounted thereon having a high spatial power density so that the resulting illumination is sufficiently intense and uniform to achieve the required projection brightness. Projection applications typically require a very dense arrangement of LED chips such as, about 237 LED chips/cm$^2$. Such high density can be achieved by making substrate 172 a multilayer printed circuit board that brings the R,G,B interconnects together. Substrate 172 may include at least one temperature sensor 176 that operates to control temperature as discussed above. Module 170 is similar to module 20 described in FIG. 2 with the main exception being that the solid-state light emitters are R, G, B emitters. Module 170 is preferably mounted on an air cooled heat sink (not shown here) similar to that describe in FIG. 3 and includes drive circuitry that produces light intensity and spatial light distribution required for projection applications such as, desktop projectors. Furthermore, the R, G, B LED chips 174 and/or any optics are controlled to allow single device control.

FIG. 13b shows the addition of an optical element 178 provided adjacent to LED chips 174 to achieve color through intensity. Optical element 178 converts LED single wavelength light into multiple wavelengths of light depending on the intensity of LED light output 179 intensity so that two, three, or more different wavelengths can be obtained from optical element 178. If desired, each LED chip 174 may be individually intensity controlled; however, individual control of each LED chip 174 is not required. Light output may be R,G,B, and light conversion may or may not be by phosphor layers.

Figure 14:
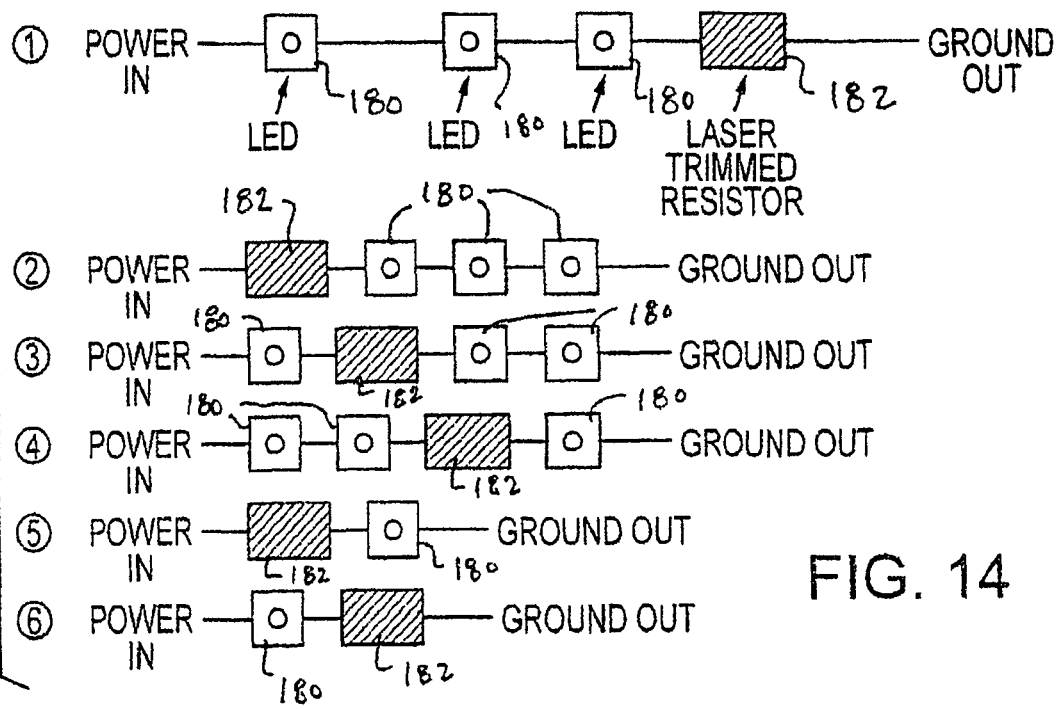
FIG. 14 shows a method of balancing and controlling the light intensity variations across the LED array.

FIG. 14 shows methods of balancing and controlling the light intensity variations across the LED array. This feature may be added (if required) to all embodiments described herein. Light output of LED or series of LEDs are controlled by varying line resistance of DC current flow. Control of current flow will control LED light output intensity. Varying intensity provides the ability to balance light intensity evenly over an LED array. Varying intensity allows control over the LED array light output to achieve non-uniform light intensity. In a first illustrated method, LEDs 180 are arranged in a series with a laser trim resistor 182 anywhere in the series. In a second illustrated method, the circuit current carrying ability inside the LED array is varied. This may be achieved by varying the size of the wire bonding the LEDs 180 to the substrate. Wire is available in varying diameter (for example, 0.001 in., 0.002 in., and 0.003 in. gold wire). Resistance of the power circuit may be controlled by varying the printed circuit board trace width and/or plated thickness. Additionally, different LEDs can have different traces as needed to control current flow. Alternatively, the LEDs can be controlled using a programmable current source implemented as a transistor-based circuit to balance the current among arrays of LEDs connected in series, and/or to arrays of LEDs arranged in rows and columns. The current source may also be implemented as a programmable current output power supply.

Figure 15:
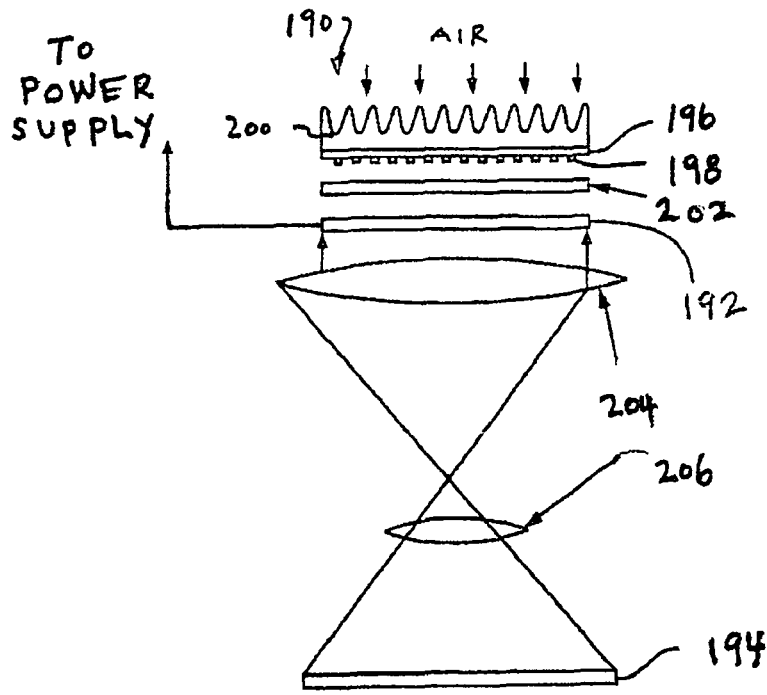
FIG. 15 shows an embodiment of the present invention for projection lithography where an image on a mask is projected onto a photopolymer forming a positive or negative image of the mask in the cured photopolymer.

FIG. 15 shows one possible embodiment of the present invention for projection lithography where a module 190 projects an image on a mask or liquid crystal display 192 onto a photopolymer work object 194 forming a positive or negative image of the mask in the cured photopolymer. Projection lithography requires a very uniform light source. Module 190 includes a substrate 196 with a dense array of LED chips 198 and an air cooled heat sink 200 as discussed above. LED chips that produce a wavelength capable of performing a projection process at a power density output of greater than 50 mW/cm$^2$ are commercially available. One skilled in the art may select a LED chip depending on its wavelength output for a specific projection application. A collimation optic element 202 may be provided to collimate light output from the LED array and either a reducing optic 204 or an enlarging optic 206 is provided depending on the size of the image to be projected. Optical element 202 is connected to a power source (not shown) in a manner similar to the connected shown and described with reference to FIGS. 4-6.

Figure 16:
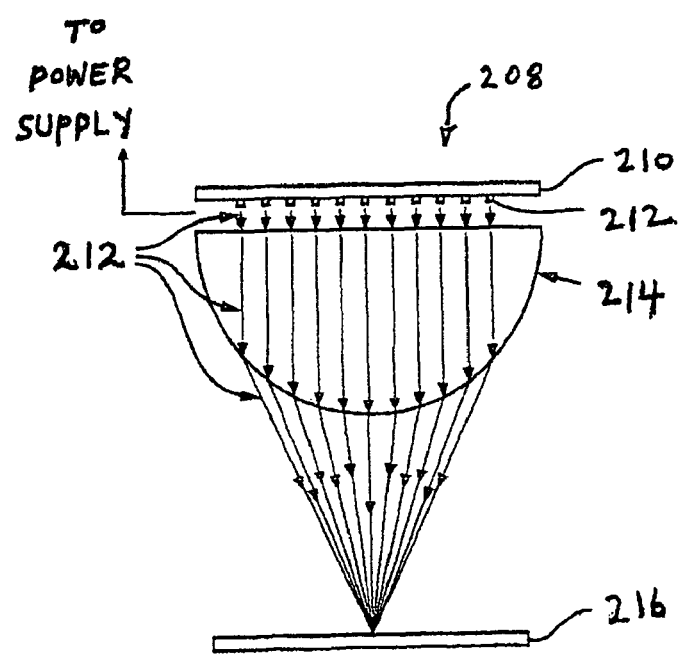
FIG. 16 shows an embodiment of the present invention for cleaning and surface modification where the maximum semiconductor light intensity is further magnified by both optical magnification and pulsing techniques to achieve power densities sufficient for ablation, disassociation, and other effects.

FIG. 16 shows one possible embodiment of the present invention for cleaning and surface modification where the maximum semiconductor light intensity is further magnified by both optical magnification and pulsing techniques to achieve power densities sufficient for ablation, disassociation, and other effects. A module 208 includes a substrate 210 with a dense array of LED chips 212 having a power supply similar to that discussed with reference to FIGS. 4-6. A single or multiple lens 214 is provided to achieve linear magnification of light output 212 from module 208 to perform an operation on a work object 216.

The lighting module of the present invention may be utilized in a variety of applications that require high-intensity ultraviolet light. For example, the lighting module may be used in fluorescence applications for mineral, polymer, and medical inspection and measurement by using a power output density of between 10-20 mW/cm$^2$ of light of a wavelength of less than about 400 nm applied for at least a duration of about 40 msec. For water sterilization, a power output density of between 2-42 mW/cm$^2$ of light of a wavelength of about 254 nm may be provided and for sterilization of blood a power output density of about 80 mW/cm$^2$ of light of a wavelength of between 325-390 nm. In polymer curing of, for example, adhesives, paints, inks, seals, conformal coatings, and masks, a power output density of between 30-300 mW/cm$^2$ of light of a wavelength of between about 300-400 nm. For imaging exposure for, for example, circuits and printing, a power output density of between 25-300 mW/cm² of light of wavelengths of about 246 nm, 365 nm, 405 nm, and 436 nm is provided for a duration of between about 6-30 seconds. In stereo lithography applications for rapid prototyping, a power output density of greater than 10 mJ/cm² of light of wavelengths between about 325-355 nm is provided for a duration of about 20 nsec. For organic cleaning applications for debris removal of, for example, epoxy or fingerprints, a power density output of between 60-500 mJ/cm² of light of wavelengths of 172 nm and 248 nm for a duration of 20 nsec. In photo ablation applications for material removal, a power output density of 1 E7 W/cm² of light of a wavelength less than about 400 nm is utilized for a duration of about 20 nsec. The light might be pulsed by drive circuits and optical elements may provide an improvement of directionality and uniformity, perhaps with gradient index planar lens materials.

In applications in which the module is used for projection the module may be used to drive fluorescing material to generate the required R,G,B output. For example, three phosphors may be used as a target and one or more phosphors may be activated depending on the intensity of the light output. This application may be used to create visual interest or for small televisions. The present invention also contemplates embodiments of the invention for deformable mirror device (DMD) and LCD based projection devices, which would overcome the problem of light output balancing from R,G,B LEDs.

Additionally, a variety of other applications including water treatments including splitting, disinfecting, ionizing, and reduction of pollutants; polymerization of medical coatings, conductive inks, controlled release drugs, and furniture coating; sterilization of medical devices, blood products, medicines, and airborne particulates; diagnostic and therapeutic uses of light for dental, skin treatment for a variety of diseases, mental disorders, and identifying particular materials through spectrographic or chromatography methods; agricultural uses including stimulating plant growth or preparing plant transitions from artificial to natural sunlight; environmental applications including the degradation of materials to accelerate biodegration.

In exposure applications, higher coherence, spectral purity, and/or directionality of light could be achieved by including an anti-reflective coated side enclosures for each LED or diode to avoid side reflections and interference effect. This will effectively prevent creative and/or destructive interferences from up close. Alternatively, the modules can be enclosed in a series of reflectors to dramatically increase the distance to the work surface to ensure greater spectral purity. Alternatively, a micro lenses could be fabricated on the LED pitch spacing to improve collimation. Such lenses might be, for example, gradient index diffractive optics or Fresnel lenses. Furthermore, distributed Bragg Reflectors formed by dielectric coatings could form a resonant cavity, which would improve light directionality. Additionally, a planar collimator, such as an assembly of one or more stacked laminated transparent materials of varying index of refraction formed in any combination, or a gradient index modified glass, perhaps assembled on the LED pitch spacing.

Figure 17:
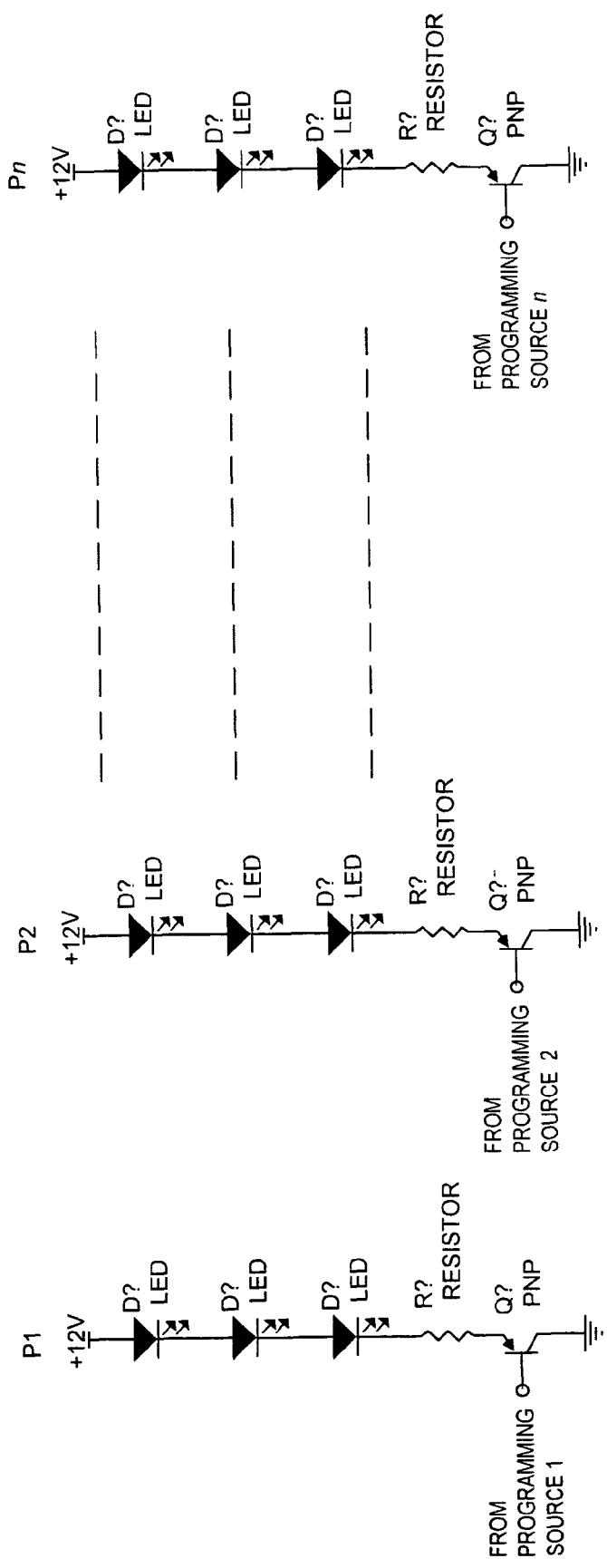
FIG. 17 is a schematic of a power control in which individual lines of the array may be controlled.

In the embodiments herein described, a power source may be constructed and arranged as seen in FIG. 17 wherein each line of LEDs in an array is powered from a separate programming source for sequencing or to vary the power to each line.

Figure 18:
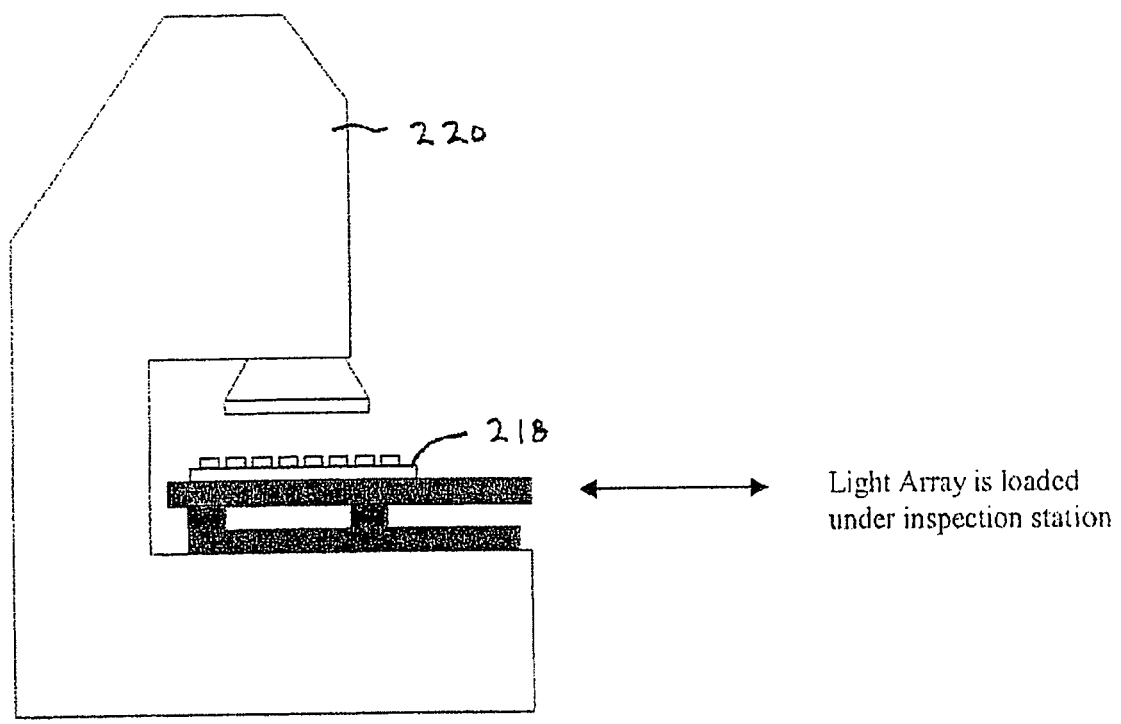
FIGS. 18 and 19 are views of a machine visions inspection device for measuring and testing the light output intensity of a solid-state light device of the present invention.
Figure 19:
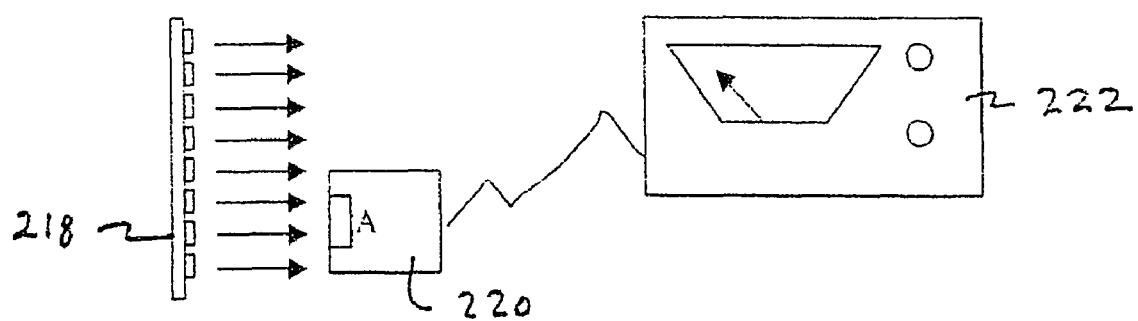

The power density output of the modules can be tested using a machine vision inspection technique, as seen in FIGS. 18 and 19, where the individual intensity of each light module is measured. This is accomplished by placing a module 218 under an inspection camera 220 such as that shown and described in published U.S. application US2002/0053589, filed Oct. 2, 2001, incorporated herein by reference. The camera aperture A (FIG. 19) is set so that light output of the module results in pixel gray scale values less than 255. The location and region of interest of each individual solid-state light emitter is defined and the intensity of each solid-state light emitter is measured. The output intensity of all of the solid-state light emitters are digitally imaged and algorithms are used to measure overall output performance of each module to identify any elements that are not working. Camera 220 measures light balancing, light distribution, and overall intensity of each module. As discussed above, power density used herein is in mW/cm2. Power density may be measured at the work surface or at the exit of the light source and is typically measured through optical elements. An average power meter 222 with an appropriately sensitive detector at the wavelength of the light source is set up with the camera aperture opening so that the light output from the source is larger in area than the diameter of the aperture. The total average power into meter 222 within the aperture opening is recorded on meter 222. The optical power density for any area of the LED array is then the ratio of the measured power on the meter in mW and area of detector in cm². Each light source in array is given it's own area of interest and is measured for it's intensity, simultaneously all of them and the relative intensity of each one to the overall is verified.

Persons skilled in the art will recognize that many modifications and variations are possible in the details, materials, and arrangements of the parts and actions which have been described and illustrated in order to explain the nature of this invention and that such modifications and variations do not depart from the spirit and scope of the teachings and claims contained therein.

The invention claimed is:

1. A lighting fixture, comprising:
    an array of solid-state light emitters including at least two modules, each module having a module array of multiple light emitters on a substrate, the substrates being electrically insulative and thermally conductive, the array mounted in the housing, wherein the solid-state light emitters are arranged on the substrates with a spacing determined by a required power density of a desired operation;
    a transistor-based current source within the housing electrically coupled to the array of solid-state light emitters, the current source receiving power from a power supply and balancing DC current between light-emitters in each module array and among the modules arrays;
    a heat sink attached to the housing arranged to dissipate heat from the array of solid-state light emitters; and
    drive circuitry within the housing to control operation of the solid-state light emitters.

2. The lighting module of claim 1, further comprising a temperature sensor located within the housing.

3. The lighting module of claim 2, the temperature sensor electrically connected to the power supply through control circuitry.

4. The lighting module of claim 2, further comprising a temperature sensor read circuit.

5. The lighting module of claim 1, wherein the housing comprises a thermally conductive material.

6. The lighting module of claim 1, further comprising a fan arranged to blow air across the heat sink.

7. The lighting module of claim 1, further comprising a liquid channel thermally coupled to the heat sink.

8. The lighting module of claim 1, further comprising the multiple substrates arranged in a line to form a light bar.

9. The lighting module of claim 8, further comprising a motive means to move the light bar relative to a work surface.

* * * * *